(12) United States Patent
Uchida

(10) Patent No.: US 11,219,356 B2
(45) Date of Patent: Jan. 11, 2022

(54) STEREOSCOPIC-VISION ENDOSCOPE

(71) Applicant: OLYMPUS CORPORATION, Tokyo (JP)

(72) Inventor: Yoshihiro Uchida, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 434 days.

(21) Appl. No.: 16/295,522

(22) Filed: Mar. 7, 2019

(65) Prior Publication Data

US 2019/0200847 A1 Jul. 4, 2019

Related U.S. Application Data

(63) Continuation of application No. PCT/JP2016/076794, filed on Sep. 12, 2016.

(51) Int. Cl.
*A61B 1/00* (2006.01)
*G02B 23/26* (2006.01)
*A61B 1/055* (2006.01)
*G02B 21/22* (2006.01)
*G02B 23/24* (2006.01)
(Continued)

(52) U.S. Cl.
CPC ...... *A61B 1/00193* (2013.01); *A61B 1/00045* (2013.01); *A61B 1/055* (2013.01); *A61B 1/06* (2013.01); *G02B 21/22* (2013.01); *G02B 23/243* (2013.01); *G02B 23/2415* (2013.01); *G02B 23/2461* (2013.01); *G02B 23/26* (2013.01); *A61B 1/0005* (2013.01);
(Continued)

(58) Field of Classification Search
CPC .................................................. A61B 1/00193

USPC ........................................................ 348/45
See application file for complete search history.

(56) References Cited

U.S. PATENT DOCUMENTS 5,612,816 A 3/1997 Strahle et al.
2002/0054431 A1* 5/2002 Costales ................ G02B 30/25
359/462

FOREIGN PATENT DOCUMENTS

JP H06167658 A 6/1994
JP H08056891 A 3/1996
JP 3290824 B2 3/2002

OTHER PUBLICATIONS

English translation of International Preliminary Report on Patentability dated Mar. 21, 2019, together with the Written Opinion received in related International Application No. PCT/JP2016/076794.

(Continued)

*Primary Examiner* — Jeffery A Williams
(74) *Attorney, Agent, or Firm* — Scully, Scott, Murphy & Presser, P.C.

(57) ABSTRACT

A stereoscopic-vision endoscope includes an objective optical system, a relay optical system, a first lens unit, a light-beam splitting element, a second lens unit, and an image sensor. An intermediate image, a first image, and a second image are formed in a common optical path, a first optical path, and a second optical path respectively. The light-beam splitting element has a surface of incidence and a surface of emergence. A first light ray which passes through the intermediate image and reaches first image and a second light ray which passes through the intermediate image and reaches the second image are refracted to be away from an optical axis of the common optical path on the surface of incidence, as well as are refracted to be closer to the optical axis of the common optical path on the surface of emergence.

25 Claims, 20 Drawing Sheets

(51) Int. Cl.
*A61B 1/06* (2006.01)
*A61B 1/04* (2006.01)
(52) U.S. Cl.
CPC ......... *A61B 1/00009* (2013.01); *A61B 1/0019* (2013.01); *A61B 1/00096* (2013.01); *A61B 1/04* (2013.01)

(56) References Cited

OTHER PUBLICATIONS

International Search Report and Written Opinion dated Nov. 15, 2016 issued in PCT/JP2016/076794.

* cited by examiner

FIG. 14A
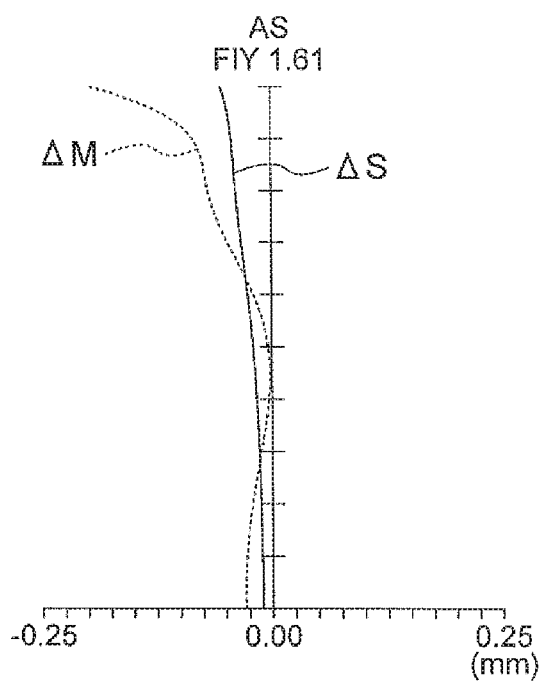
FIG. 14B
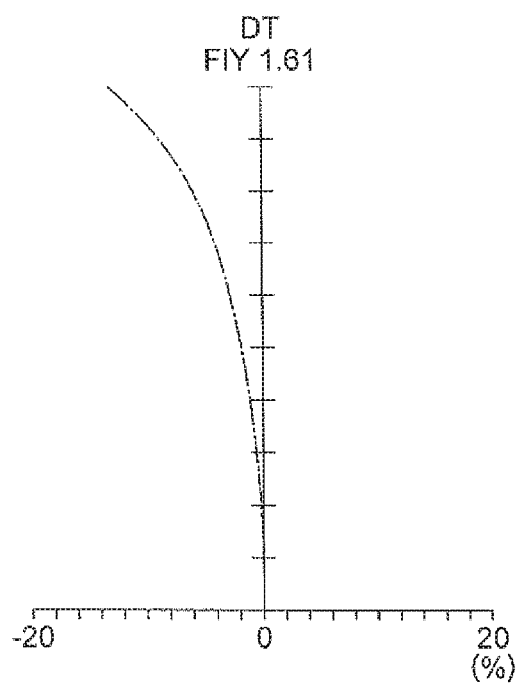
FIG. 14C 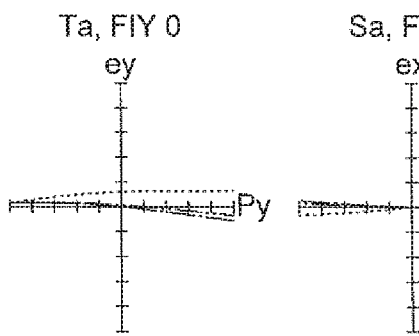 FIG. 14D 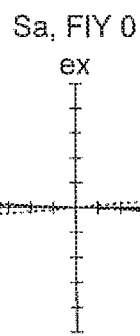 FIG. 14E FIG. 14F 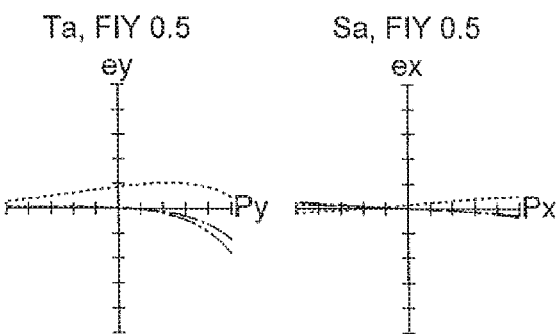 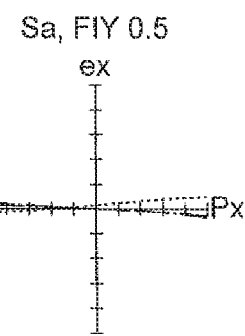
FIG. 14G 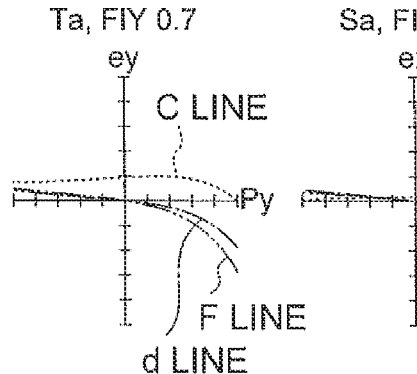 FIG. 14H 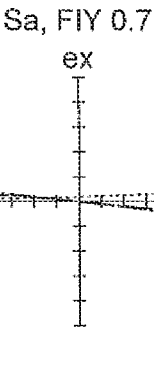 FIG. 14I FIG. 14J 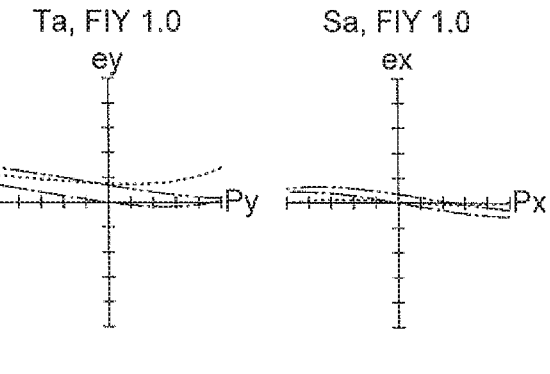 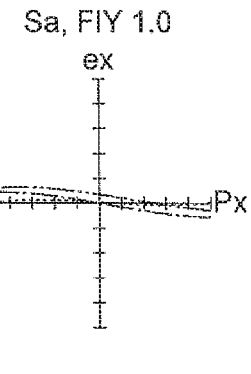
---- 0.486
--- 0.588
------ 0.656

AS
FIY 1.61

DT
FIY 1.61

Ta, FIY 0
ey

Sa, FIY 0
ex

Ta, FIY 0.5
ey

Sa, FIY 0.5
ex

Ta, FIY 0.7
ey

Sa, FIY 0.7
ex

Ta, FIY 1.0
ey

Sa, FIY 1.0
ex

AS FIY 1.61

-0.25 0.00 0.25 (mm)

DT FIY 1.61

-20 0 20 (%)

FIG. 16C Ta, FIY 0 ey ... Py
FIG. 16D Sa, FIY 0 ex ... Px
FIG. 16E Ta, FIY 0.5 ey ... Py
FIG. 16F Sa, FIY 0.5 ex ... Px

FIG. 16G Ta, FIY 0.7 ey ... Py
FIG. 16H Sa, FIY 0.7 ex ... Px
FIG. 16I Ta, FIY 1.0 ey ... Py
FIG. 16J Sa, FIY 1.0 ex ... Px

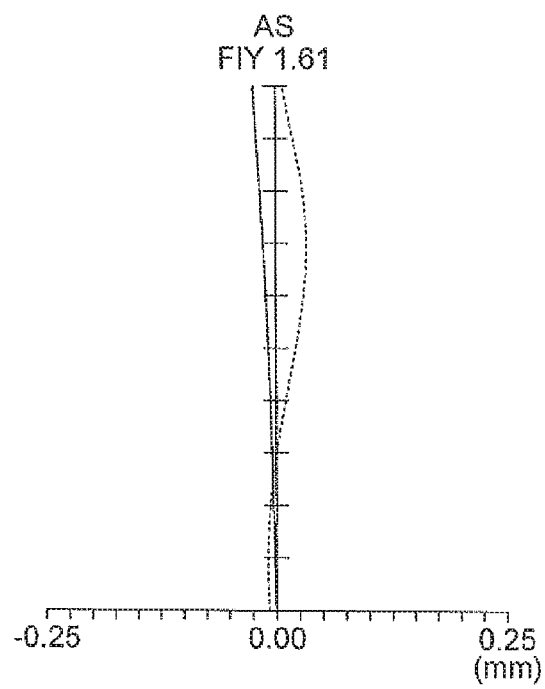
FIG. 18A
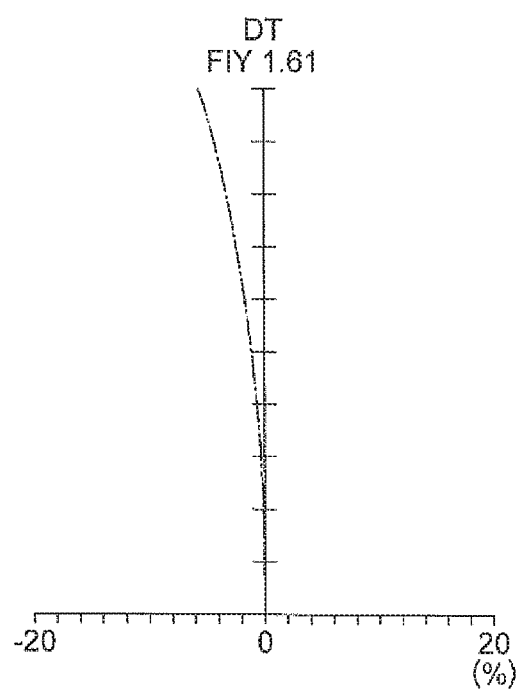
FIG. 18B
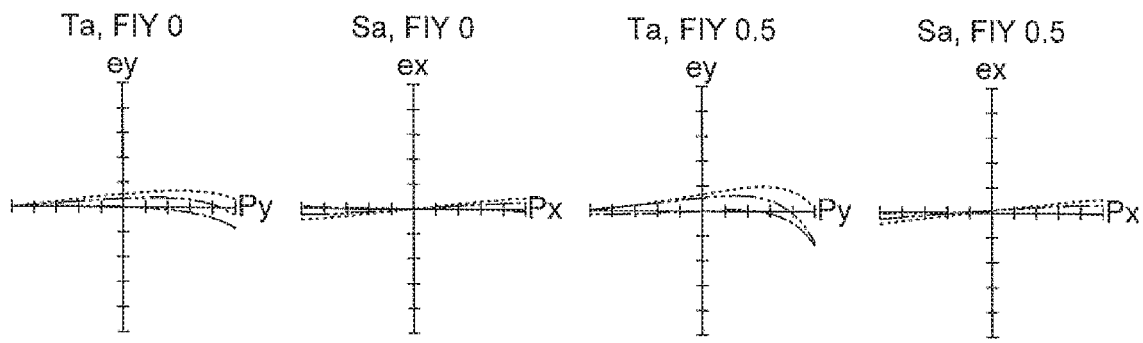
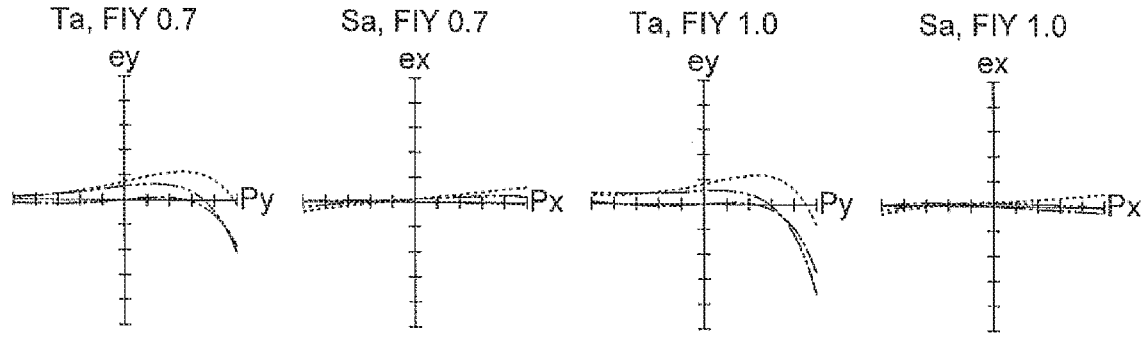

FIG. 19A
FIG. 19B
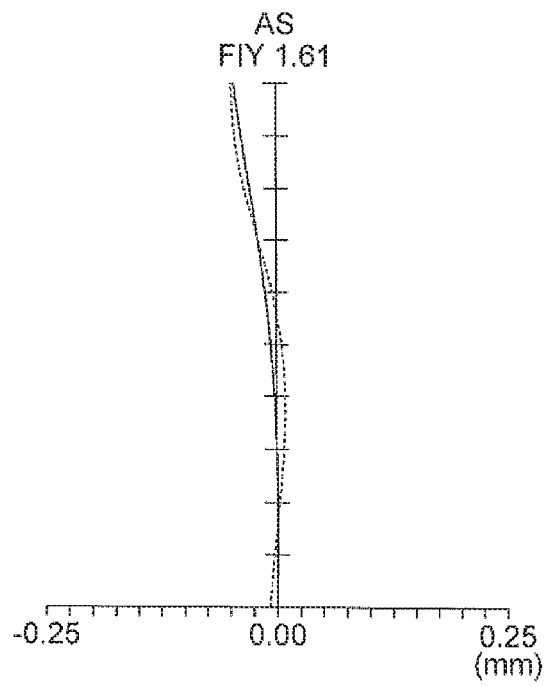
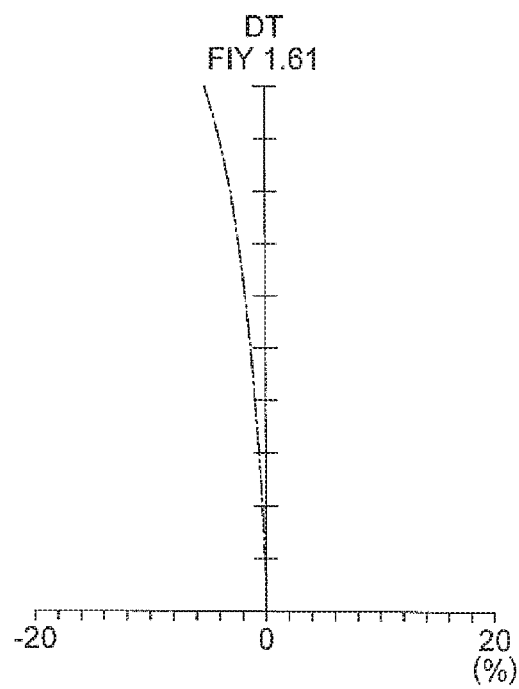
FIG. 19C  FIG. 19D  FIG. 19E  FIG. 19F
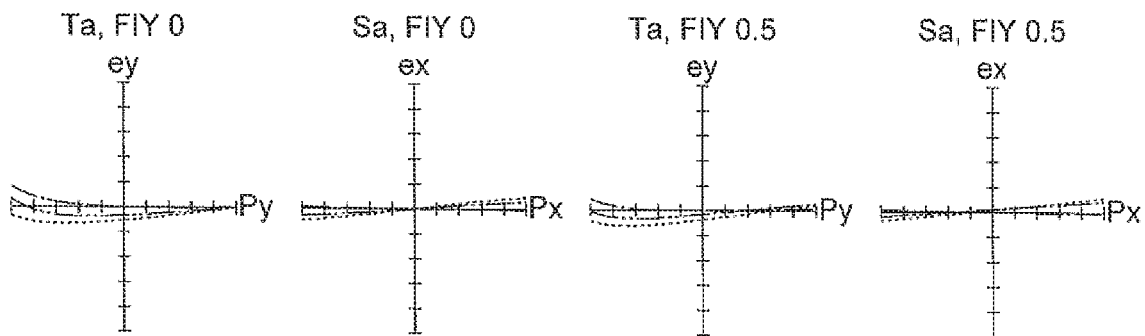
FIG. 19G  FIG. 19H  FIG. 19I  FIG. 19J
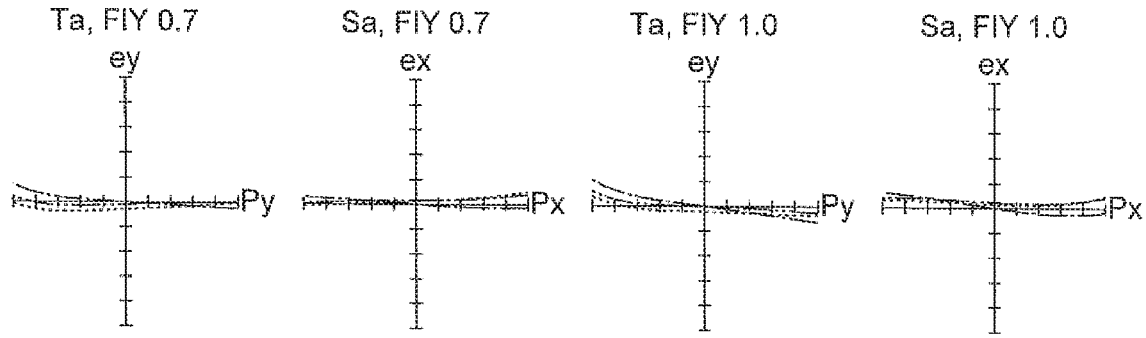

STEREOSCOPIC-VISION ENDOSCOPE

CROSS-REFERENCE TO RELATED APPLICATION

The present application is a continuation application of International Application No. PCT/JP2016/076794 filed on Sep. 12, 2016, the entire contents of which are incorporated herein by reference.

BACKGROUND OF THE INVENTION

Field of the Invention

The present invention relates to a stereoscopic-vision endoscope which enables stereoscopic observation of an object.

Description of the Related Art

As an optical system to be used in a stereoscopic-vision endoscope for medical treatment, an optical system equipped with an objective optical system and a relay optical system has hitherto been known. In this optical system, an objective lens is disposed at a front end of an insertion portion of an endoscope. The relay optical system is also disposed in the insertion portion, and relays an image of the objective optical system. An image relayed is transmitted to an optical system such as an observation optical system and an image pickup optical system provided outside the insertion portion.

In Japanese Patent No. 3290824 Publication, an optical system to be used in a stereoscopic-vision endoscope has been disclosed. In this optical system, an objective optical system and a relay optical system are disposed in a common optical path. A pupil has been divided on an image side of the relay optical system. Accordingly, two images are formed in different spaces.

In an optical system of an example 1, a stop is disposed on the image side of the relay optical system. The stop has two apertures formed therein at positions away from an optical axis of the common optical path. Accordingly, two optical paths are formed on an image side of the stop. A separation optical system and an image pickup element are disposed in each of the two optical paths.

In an optical system of an example 3, an axial-spacing enlargement optical system is disposed between a stop and a separation optical system. As the axial-spacing enlargement optical system, an optical system that uses reflection and an optical system that uses only refraction have been disclosed.

SUMMARY OF THE INVENTION

A stereoscopic-vision endoscope according to at least some embodiments of the present invention comprises in order from an object side,
an objective optical system,
a relay optical system,
a first lens unit,
a light-beam splitting element,
a second lens unit, and
an image sensor, wherein
the objective optical system, the relay optical system, the first lens unit, and the light-beam splitting element are disposed in a common optical path, and a first optical path and a second optical path are formed on an image side of the light-beam splitting element, by the light-beam splitting element, and
the second lens unit is disposed in each of the first optical path and the second optical path, and
an image of an object is formed by the objective optical system, and
the image of the object is relayed by the relay optical system, and
an intermediate image is formed on the object side of the first lens unit by the relay optical system, and
a first image is formed by the first lens unit and the second lens unit which is disposed in the first optical path, and
a second image is formed by the first lens unit and the second lens unit which is disposed in the second optical path, and
the first image and the second image are captured by the image sensor, and
the light-beam splitting element has a surface of incidence and a surface of emergence, and
a first light ray which passes through a center of the intermediate image and reaches a center of the first image and a second light ray which passes through the center of the intermediate image and reaches a center of the second image are refracted to be away from an optical axis of the common optical path on the surface of incidence, as well as are refracted to be closer to the optical axis of the common optical path on the surface of emergence.

BRIEF DESCRIPTION OF THE DRAWINGS

FIG. 14A, FIG. 14B, FIG. 14C, FIG. 14D, FIG. 14E, FIG. 14F, FIG. 14G, FIG. 14H, FIG. 14I, and FIG. 14J (hereinafter, FIG. 14A to FIG. 14J) are aberration diagrams of the optical system for endoscope of the example 1;

FIG. 16A, FIG. 16B, FIG. 16C, FIG. 16D, FIG. 16E, FIG. 16F, FIG. 16G, FIG. 16H, FIG. 16I, and FIG. 16J (hereinafter, FIG. 16A to FIG. 16J) are aberration diagrams of the optical system for endoscope of the example 2;

FIG. 18A, FIG. 18B, FIG. 18C, FIG. 18D, FIG. 18E, FIG. 18F, FIG. 18G, FIG. 18H, FIG. 18I, and FIG. 18J (hereinafter, FIG. 18A to FIG. 18J) are aberration diagrams of the optical system for endoscope of the example 3;

FIG. 19A, FIG. 19B, FIG. 19C, FIG. 19D, FIG. 19E, FIG. 19F, FIG. 19G, FIG. 19H, FIG. 19I, and FIG. 19J (hereinafter, FIG. 19A to FIG. 19J) are aberration diagrams of the optical system for endoscope of the example 3.

DETAILED DESCRIPTION OF THE INVENTION

Prior to the explanation of examples, action and effect of embodiments according to certain aspects of the present invention will be described below. In the explanation of the action and effect of the embodiments concretely, the explanation will be made by citing concrete examples. However, similar to a case of the examples to be described later, aspects exemplified thereof are only some of the aspects included in the present invention, and there exists a large number of variations in these aspects. Consequently, the present invention is not restricted to the aspects that will be exemplified.

A stereoscopic-vision endoscope of the present embodiment includes in order from an object side, an objective optical system, a relay optical system, a first lens unit, a light-beam splitting element, a second lens unit, and an image pickup element, wherein the objective optical system, the relay optical system, the first lens unit, and the light-beam splitting element are disposed in a common optical path, and a first optical path and a second optical path are formed on an image side of the light-beam splitting element, by the light-beam splitting element, and the second lens unit is disposed in each of the first optical path and the second optical path, and an image of an object is formed by the objective optical system, and the image of the object is relayed by the relay optical system, and an intermediate image is formed on the object side of the first lens unit by the relay optical system, and a first image is formed by the first lens unit and the second lens unit which is disposed in the first optical path, and a second image is formed by the first lens unit and the second lens unit which is disposed in the second optical path, and the first image and the second image are captured by the image pickup element, and the light-beam splitting element has a surface of incidence and a surface of emergence, and a first light ray which passes through a center of the intermediate image and reaches a center of the first image and a second light ray which passes through the center of the intermediate image and reaches a center of the second image are refracted to be away from an optical axis of the common optical path on the surface of incidence, as well as are refracted to be closer to the optical axis of the common optical path on the surface of emergence.

Figure 1A:
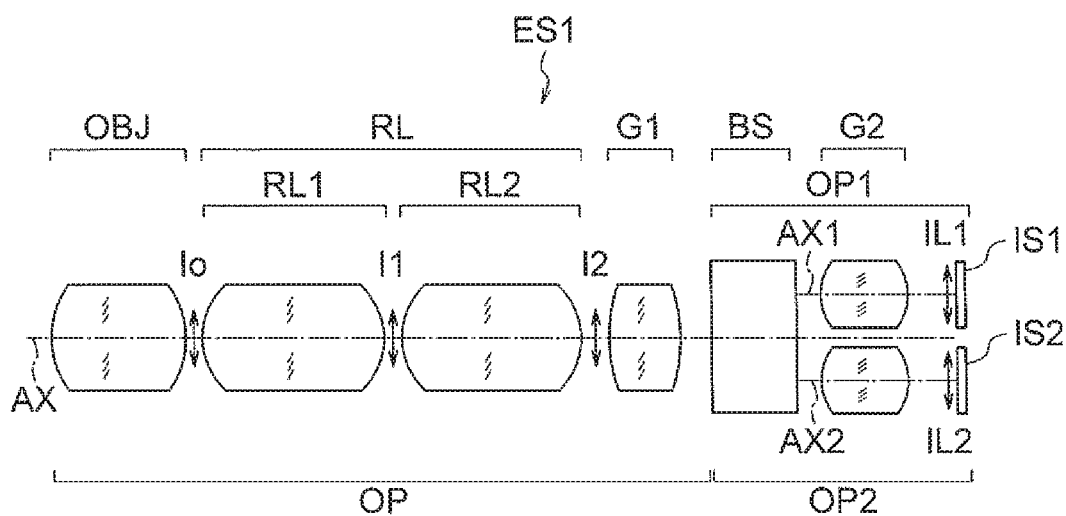
FIG. 1A and FIG. 1B are schematic structural views of a stereoscopic-vision endoscope of the present embodiment.
Figure 1B:
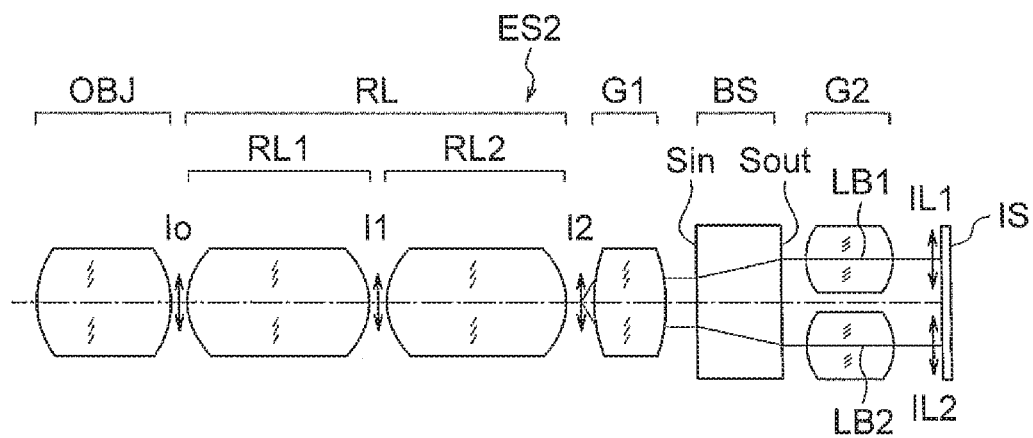

FIG. 1A and FIG. 1B are schematic structural views of the stereoscopic-vision endoscope of the present embodiment. FIG. 1A shows an arrangement in which the number of image pickup elements is two, and FIG. 1B shows an arrangement in which the number of image pickup elements is one.

Both of a stereoscopic-vision endoscope ES1 shown in FIG. 1A and a stereoscopic-vision endoscope ES2 shown in FIG. 1B include an endoscope optical system and an image pickup element. The endoscope optical system of the stereoscopic-vision endoscope ES1 and the endoscope optical system of the stereoscopic-vision endoscope ES2 are identical.

The endoscope optical system includes in order from the object side, an objective optical system OBJ, a relay optical system RL, a first lens unit G1, a light-beam splitting element BS, and a second lens unit G2.

FIG. 1A and FIG. 1B are schematic structural views. Therefore, the objective optical system. OBJ is depicted by one lens. However, practically, the objective optical system OBJ includes a plurality of lenses. Similar is true for a first relay lens RL1, a second relay lens RL2, the first lens unit G1, and the second lens unit G2.

The stereoscopic-vision endoscope ES1 includes a first image pickup element IS1 and a second image pickup element IS2. The stereoscopic-vision endoscope ES2 includes an image pickup element IS.

In the endoscope optical system, a common optical path OP, a first optical path OP1, and a second optical path OP2 are formed. The objective optical system OBJ, the relay optical system RL, the first lens unit G1, and the light-beam splitting element BS are disposed in the common optical path OP.

The first optical path OP1 and the second optical path OP2 are formed on the image side of the light-beam splitting element BS, by the light-beam splitting element BS. The first optical path OP1 and the second optical path OP2 are positioned in a direction orthogonal to an optical axis AX of the common optical path OP. The first optical path OP1 is positioned on one side of the optical axis AX and the second optical path OP2 is positioned on the other side of the optical axis AX, thus the two optical paths sandwiching the optical axis AX. The second lens unit G2 is disposed in each of the first optical path OP1 and the second optical path OP2.

Both of an optical axis AX1 of the first optical path OP1 and an optical axis AX2 of the second optical path OP2 may be parallel to the optical axis AX or may be nonparallel to the optical axis AX. In the stereoscopic-vision endoscope ES1 and the stereoscopic-vision endoscope ES2, the optical axis AX1 and the optical axis AX2 are parallel to the optical axis AX.

In the endoscope optical system, an image Io of an object is formed by the objective optical system OBJ. The relay optical system RL is disposed on the image side of the objective optical system OBJ. The image Io of the object is relayed by the relay optical system RL.

The relay optical system RL includes the first relay lens RL1 and the second relay lens RL2. A first relay image I1 is formed by the first relay lens RL1. A second relay image I2 is formed by the second relay lens RL2. The number of relay lenses is not restricted to two. The number of relay lenses may be one or may be three or more than three.

The first lens unit G1 is disposed on the image side of the relay optical system RL. By making such arrangement, it is possible to make a light-beam diameter small.

An intermediate image is formed on the object side of the first lens unit G1. An image relayed by the relay optical system RL is formed on the object side of the first lens unit G1. Accordingly, an image relayed by the relay optical system RL becomes the intermediate image. In FIG. 1A and FIG. 1B, the second relay image I2 becomes an intermediate image I2.

The light-beam splitting element BS is disposed on the image side of the first lens unit G1. As shown in FIG. 1B, the light-beam splitting element BS has a surface of incidence Sin and a surface of emergence Sout. The first optical path OP1 and the second optical path OP2 are formed on the image side of the light-beam splitting element BS, by the light-beam splitting element BS.

A first image IL1 is formed by the first lens unit G1 and the second lens unit G2 which is disposed in the first optical path OP1. A second image IL2 is formed by the first lens unit G1 and the second lens unit G2 which is disposed in the second optical path OP2.

The first image IL1 and the second image IL2 are captured by an image pickup element. In the stereoscopic-vision endoscope ES1, the first image IL1 is captured by the first image pickup element IS1 and the second image IL2 is captured by the second image pickup element IS2. In the stereoscopic-vision endoscope ES2, the first image IL1 and the second image IL2 are captured by the image pickup element IS.

As mentioned above, FIG. 1A and FIG. 1B are schematic structural views. Therefore, in FIG. 1A and FIG. 1B, the surface of incidence Sin and the surface of emergence Sout are flat surfaces orthogonal to the optical axis AX. However, practically, the surface of incidence Sin and the surface of emergence Sout are not flat surfaces orthogonal to the optical axis AX. Therefore, when a light ray passes through the light-beam splitting element BS, a position of incidence on the surface of incidence Sin and a position of emergence on the surface of emergence Sout differ.

A refraction of a light ray advancing along the first optical path OP1 and a refraction of a light ray advancing along the second optical path OP2 will be described below. Light rays passing through a center of the intermediate image I2 and reaching a center of the first image IL1 exist in plurality. Similarly, light rays passing through a center of the intermediate image I2 and reaching a center of the second image IL2 exist in plurality.

Therefore, in the description, a light ray advancing along the optical axis AX1 of the first optical path OP1 (hereinafter, referred to as 'first light ray LB1') and a light ray advancing along the optical AX2 of the second optical path OP2 (hereinafter, referred to as 'second light ray LB2') will be used.

The first light ray LB1 is refracted at the surface of incidence Sin. Due to the refraction, the first light ray LB1 goes away from the optical axis AX. The first light ray LB1 is refracted at the surface of emergence Sout. Due to the refraction, the first light ray LB1 comes closer to the optical axis AX.

The second light ray LB2 is refracted at the surface of incidence Sin. Due to the refraction, the second light ray LB2 goes away from the optical axis AX. The second light ray LB2 is refracted at the surface of emergence Sout. Due to the refraction, the second light ray LB2 comes closer to the optical axis AX.

In such manner, the first light ray LB1 and the second light ray LB2 are refracted to go away from the optical axis AX at the surface of incidence Sin as well as are refracted to come closer to the optical axis AX at the surface of emergence Sout.

By making such arrangement, it is possible to maintain a distance between the first image IL1 and the second image IL2 while securing a parallax appropriately. Furthermore, it is possible to cancel an asymmetric aberration which occurs at the surface of incidence Sin, at the surface of emergence Sout. Consequently, it is possible to secure a favorable resolution performance while small-sizing the optical system.

In the stereoscopic-vision endoscope ES1 and the stereoscopic-vision endoscope ES2, the first image IL1 and the second image IL2 are shifted with respect to the intermediate image I2. Moreover, the two second lens units G2 are shifted with respect to the first lens unit G1. Therefore, the optical axis AX1 and the optical axis AX2 are to be made parallel to the optical axis AX, and an amount of shift with respect to and image and an amount of shift with respect to a lens are to be let to be about same amount. By making such arrangement, it is possible to suppress more effectively an occurrence of a decentering aberration.

In an endoscope, it is possible to observe the intermediate image I2 by using an eyepiece optical system. Therefore, a part of or the whole of the first lens unit G1 may be replaced by an eyepiece optical system.

In the stereoscopic-vision endoscope of the present embodiment, it is preferable that the following conditional expression (1) be satisfied:

$$-0.1 \leq (FLBSout - FLBSin)/(FLBSout + FLBSin) \leq 0.1 \quad (1)$$

where,

FLBSin denotes a focal length at the surface of incidence of the light-beam splitting element, and FLBSout denotes a focal length at the surface of emergence of the light-beam splitting element.

In the light-beam splitting element, it is preferable that the focal length of the surface of incidence and the focal length of the surface of emergence be same. By satisfying conditional expression (1), it is possible to almost cancel an asymmetric aberration that occurs at the surface of incidence, by an aberration that occurs at the surface of emergence. Accordingly, it is possible to suppress the asymmetric aberration to be small.

In the stereoscopic-vision endoscope of the present embodiment, it is preferable that the following conditional expressions (2) and (3) be satisfied:

$$-0.01 \leq Yimg/FLBSin \leq 0.01 \quad (2)$$

$$-0.01 \leq Yimg/FLBSout \leq 0.01 \quad (3)$$

where,

FLBSin denotes the focal length at the surface of incidence of the light-beam splitting element, FLBSout denotes the focal length at the surface of emergence of the light-beam splitting element, and Yimg denotes the maximum image height.

Conditional expression (2) is a conditional expression related to the maximum image height and the focal length of the surface of incidence of the light-beam splitting element. Conditional expression (3) is a conditional expression related to the maximum image height and the focal length of the surface of emergence of the light-beam splitting element.

Figure 2A:
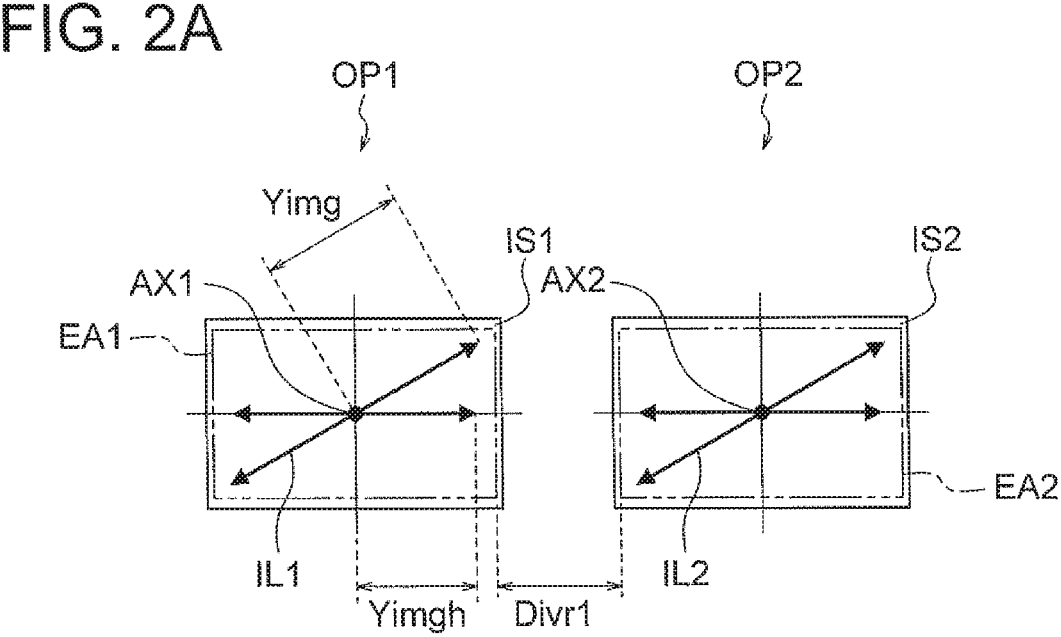
FIG. 2A and FIG. 2B are diagrams showing an image formed on an image pickup element.
Figure 2B:
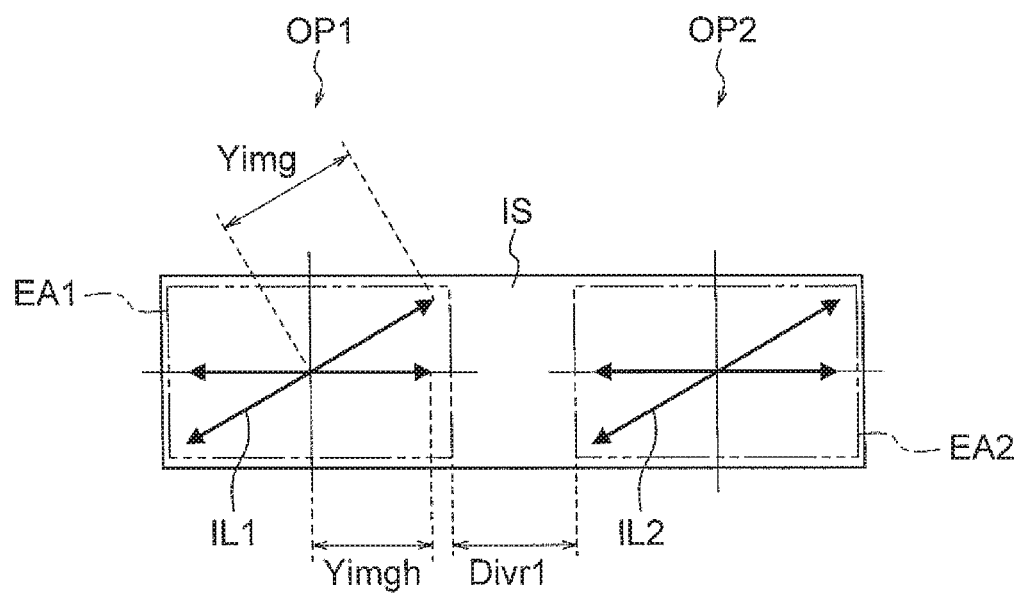

FIG. 2A and FIG. 2B are diagrams showing an image formed on the image pickup element. FIG. 2A shows a case in which the number of image pickup elements is two and FIG. 2B shows a case in which the number of image pickup elements is one. The image pickup element (image sensor) includes a plurality of photoelectric conversion portions. As the image pickup element, CCD or CMOS can be used.

In the case in which the number of image pickup elements is two, the first image IL1 is formed on an image pickup surface of the first image pickup element IS1 and the second image IL2 is formed on an image pickup surface of the second image pickup element IS2. Here, the description will be made by citing the first image pickup element IS1, as an example. The first image pickup element IS1 has a first effective area EA1 shown by an alternate long and two short dashes line.

The maximum image height is the image height which is the maximum among heights of image formed in the effective area. The first effective area EA1 being rectangular-shaped, an image height in a diagonal direction becomes the maximum image height. In a case in which the effective area is circular-shaped, the image height being same in any direction, an image height in an arbitrary direction becomes the maximum image height. Similar is true for the image pickup element IS2 and the image pickup element IS.

In the light-beam splitting element, it is preferable that both the surface of incidence and the surface of emergence almost do not have the refractive power. By satisfying conditional expressions (2) and (3), it is possible to suppress an occurrence of an asymmetric aberration at the surface of incidence and an occurrence of an asymmetric aberration at the surface of emergence.

It is possible to make the focal length at the surface of incidence 1000 mm for example. By making such arrangement, in the light-beam splitting element, it is possible to suppress a light-ray height to be low. In the light-beam splitting element, it is desirable that both the surface of incidence and the surface of emergence be flat surfaces.

In the stereoscopic-vision endoscope of the present embodiment, it is preferable that the image pickup element have a first effective area capturing the first image, and a second effective area capturing the second image, and the following conditional expression (4) be satisfied:

$$0.05 \leq Divlr/Yimgh \leq 2 \quad (4)$$

where,

Divlr denotes the minimum distance between the first effective area and the second effective area, and Yimgh denotes a predetermined image height, and here the minimum distance is a distance which is the smallest distance between a point on an outer periphery of the first effective area and a point on an outer periphery of the second effective area, the predetermined image height is a height when the maximum image height is projected in a parallax direction, the distance is a distance in the parallax direction, and the parallax direction is a direction orthogonal to both of an optical axis of the first optical path and an optical axis of the second optical path.

Conditional expression (4) is a conditional expression related to the minimum distance between the first effective area and the second effective area, and the predetermined image height.

The minimum distance between the first effective area and the second effective area is a distance which is the smallest among distances between the first effective area and the second effective area. The minimum distance is determined by calculating a distance between a point on an outer periphery of the first effective area and a point on an outer periphery of the second effective area, for each point, and comparing the calculated distances.

In FIG. 2A and FIG. 2B, the first effective area EA1 and the second effective area EA2 are positioned side-by-side in a leftward-rightward direction on a paper surface. Moreover, both the first effective area EA1 and the second effective area EA2 are rectangular-shaped.

The distance between a point on the outer periphery of the first effective area EA1 and a point on the outer periphery of the second effective area EA2 is compared for each point. A left side of the second effective area EA2 is nearest to a right side of the first effective area EA1. Therefore, a distance between the right side of the first effective area EA1 and the left side of the second effective area EA2 becomes the minimum distance.

In such manner, in FIG. 2A and FIG. 2B, the distance between the right side of the first effective area EA1 and the left side of the second effective area EA2 becomes the minimum distance between the first effective area EA1 and the second effective area EA2.

The parallax occurs in a direction of shifting of the first image IL1 and the second image IL2. The shift of the first image IL1 and the shift of the second image IL2 occur in a direction orthogonal to both the optical axis AX1 and the optical axis AX2. Accordingly, the direction orthogonal to both the optical axis AX1 and the optical axis AX2 becomes the parallax direction.

In FIG. 2A and FIG. 2B, the leftward-rightward direction of the paper surface is the direction orthogonal to both the optical axis AX1 and the optical axis AX2. Therefore, the leftward-rightward direction is the parallax direction. Moreover, the predetermined image height is an image height when the maximum image height is projected in the parallax direction. Therefore, an image height in the leftward-rightward direction of the paper surface is the predetermined image height.

By making so as not to exceed an upper limit value of conditional expression (4), it is possible to maintain appropriately a proportion of a light beam along the first optical path and a proportion of a light beam along the second optical path. Accordingly, it is possible to suppress an occurrence of an asymmetric aberration and an occurrence of a coma of high order. As a result, it is possible to carry out small-sizing of the optical system while securing the favorable resolution performance.

By making so as not to fall below a lower limit value of conditional expression (4), it is possible to secure adequately an effective aperture of the second lens unit while maintaining appropriately the proportion of the light beam along the first optical path and the proportion of the light beam along the second optical path. Consequently, it is possible to suppress an occurrence of an off-axis aberration, and particularly, the coma, in the second lens unit.

In the stereoscopic-vision endoscope of the present embodiment, it is preferable that an aperture stop be disposed between the first lens unit and the light-beam splitting element or between the light-beam splitting element and the second lens unit.

By making such arrangement, it is possible to make small a size of the light-beam splitting element.

In the stereoscopic-vision endoscope of the present embodiment, it is preferable that the following conditional expression (5) be satisfied:

$$0.7 \leq Divs/(Divlr/2 + Yimgh) \leq 1.3 \quad (5)$$

where,

Divs denotes a distance between a point of incidence and a point of emergence,

Divlr denotes the minimum distance between the first effective area and the second effective area, and Yimgh denotes the predetermined image height, and here the point of incidence is a point of intersection of the first light ray and the surface of incidence, the point of emergence is a point of intersection of the first light ray and the surface of emergence, the minimum distance is the distance which is the smallest distance between the point on the outer periphery of the first effective area and the point on the outer periphery of the second effective area, the predetermined image height is the height when the maximum image height is projected in the parallax direction, the distance is the distance in the parallax direction, and the parallax direction is the direction orthogonal to both of the optical axis of the first optical path and the optical axis of the second optical path.

Conditional expression (5) is a conditional expression related to the distance between the point of incidence and the point of emergence, the minimum distance between the first effective area and the second effective area, and the predetermined image height.

Figure 3:
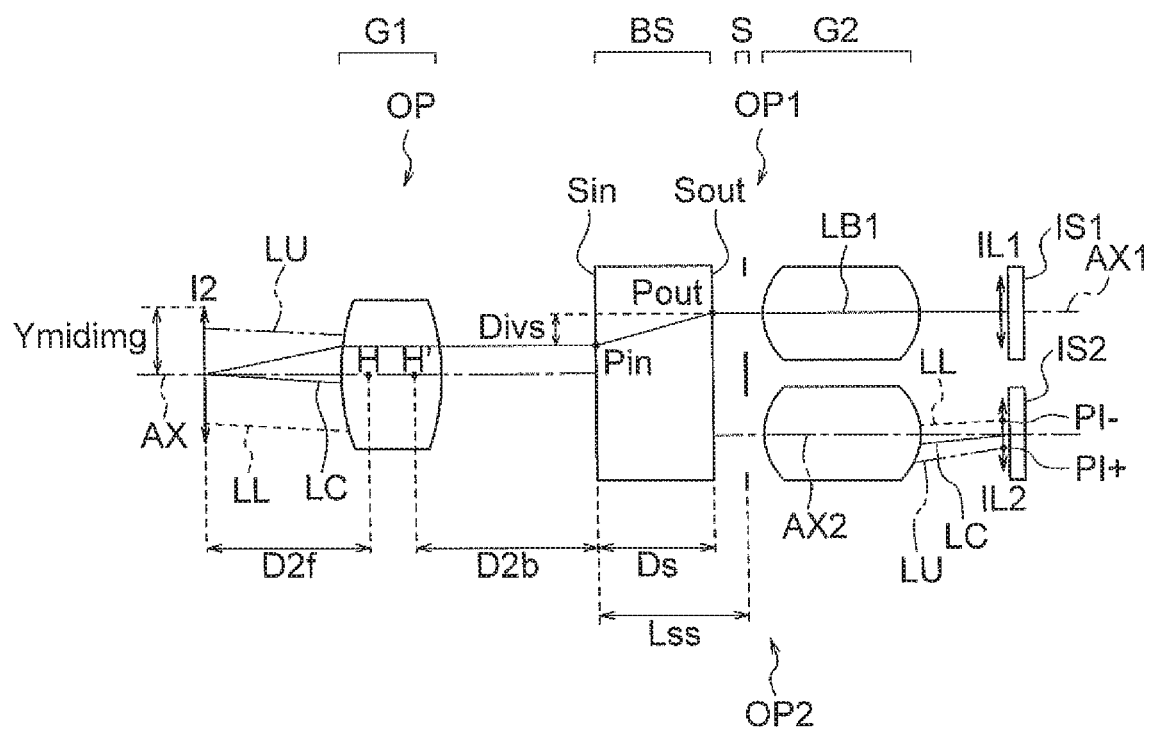
FIG. 3 is a schematic structural view of the stereoscopic-vision endoscope of the present embodiment.

FIG. 3 is a schematic structural view of the stereoscopic-vision endoscope of the present embodiment. As mentioned above, the first light ray LB1 is refracted at the surface of incidence Sin of the light-beam splitting element BS, to be away from the optical axis of the common optical path. Accordingly, when the first light ray LB1 passes through the light-beam splitting element BS, a position of incidence Pin on the surface of incidence Sin and a position of emergence Pout on the surface of emergence Sout differ.

The position of incidence Pin is a point of intersection of the first light ray LB1 and the surface of incidence Sin. Accordingly, the position of incidence Pin is the point of incidence. Moreover, the position of emergence Pout is a point of intersection of the first light ray LB1 and the surface of incidence Sout. Accordingly, the position of emergence Pout is the point of emergence.

In FIG. 3, a vertical direction of the paper surface is the direction orthogonal to both the optical axis AX1 and the optical axis AX2. In this case, the vertical direction of the paper is the parallax direction. Accordingly, a distance between the position of incidence Pin and the position of emergence Pout is the distance between the point of incidence and the point of emergence.

The point of incidence may be a point of intersection of the second light ray and the surface of incidence. Moreover, the point of emergence may be a point of intersection of the second light ray and the surface of incidence.

By making so as not to exceed an upper limit value of conditional expression (5), it is possible to maintain appropriately the proportion of the light beam along the first optical path and the proportion of the light beam along the second optical path. Accordingly, it is possible to suppress the occurrence of the asymmetric aberration and the occurrence of the coma of high order. As a result, it is possible to carry out small-sizing of the optical system while securing the favorable resolution performance.

By making so as not to fall below a lower limit value of conditional expression (5), it is possible to secure adequately the effective aperture of the second lens unit while maintaining appropriately the proportion of the light beam along the first optical path and the proportion of the light beam along the second optical path. Consequently, it is possible to suppress the occurrence of an off-axis aberration, and particularly, the coma, in the second lens unit.

It is possible to make the distance between the point of incidence and the point of emergence 0.22 mm for example. In this case, the point of intersection of the first light ray and the second light ray in an object space is at a position when the object distance is 50 mm.

By making the distance between the point of incidence and the point of emergence 0.3 mm for example, it is possible to let the point of intersection of the first light ray and the second light ray in the object space to be at a position when the object distance is 12 mm. As a result, it is possible to form an image of an object positioned at a close distance, at a position far away from an observer at a time of viewing stereoscopically, while maintaining a large angle of view of the endoscope optical system. At this time, a value in conditional expression becomes 0.97.

In the stereoscopic-vision endoscope of the present embodiment, it is preferable that the following conditional expression (6) be satisfied:

$$0.8 \leq D2f/FLG1f \leq 1.2 \tag{6}$$

where,

D2f denotes a distance on an optical axis of the common optical path, between a position of a principal point on the object side of the first lens unit and the intermediate image, and FLG1f denotes an object-side focal length of the first lens unit.

The first light beam and the second light beam, after being incidence on the light-beam splitting element, are emerged from the light-beam splitting element. In a case in which both the first light beam and the second light beam emerged from the light-beam splitting element are nonparallel to the optical axis of the common optical path, there is a difference in an optical-path length of the three light beams. As a result, a decentering aberration occurs. Therefore, it is preferable that both the first light beam and the second light beam, when emerged from the light-beam splitting element, be substantially parallel to the optical axis of the common optical path.

The three light rays will be described below. As shown in FIG. 3, the three light rays are an axial light ray LC, an upper subordinate light ray LU, and a lower subordinate light ray LL. Both the upper subordinate light ray LU and the lower subordinate light ray LL are off-axis light rays. Here, although light rays which form the second image IL2 are described, similar description is applicable to the first image IL2.

By making so as not to exceeded an upper limit value of conditional expression (6) or so as not to fall below a lower limit value of conditional expression (6), it is possible to make small a difference in the optical-path lengths for the three light rays. As a result, it is possible to suppress an occurrence of the decentering aberration due to the difference in the optical-path lengths for the three light rays.

In the stereoscopic-vision endoscope of the present embodiment, it is preferable that both the first light ray emerged from the surface of emergence and the second light ray emerged from the surface of emergence be parallel to the optical axis of the common optical path.

By making such arrangement, it is possible to suppress the occurrence of the decentering aberration more effectively.

In the stereoscopic-vision endoscope of the present embodiment, it is preferable that the surface of incidence and the surface of emergence have a shape such that a distance from the optical axis of the common optical path increases toward the object side from a point of intersection of the optical axis of the common optical path.

At the surface of incidence and the surface of emergence of the light-beam splitting element, an aberration which is asymmetric with respect to a chief ray is susceptible to occur. By making the shape of the surface of incidence and the shape of the surface of emergence as mentioned above, it is possible to suppress the occurrence of the asymmetric aberration to be small.

Figure 4:
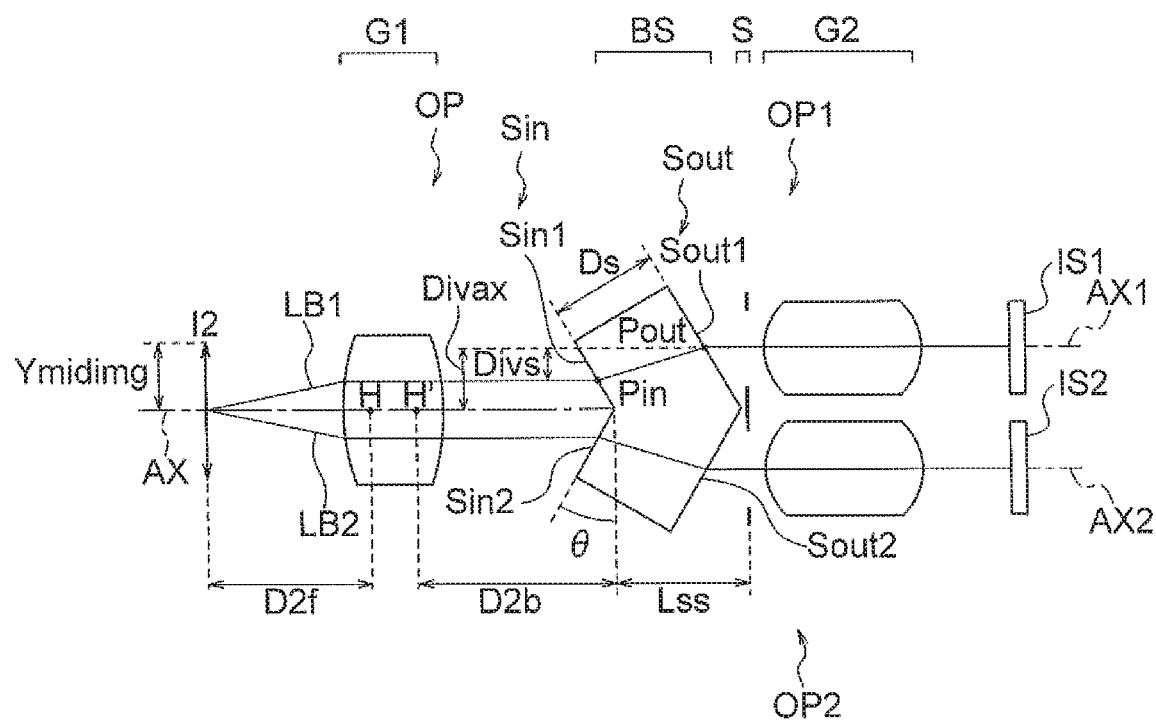
FIG. 4 is a schematic structural view of the stereoscopic-vision endoscope of the present embodiment.

FIG. 4 is a schematic structural view of the stereoscopic-vision endoscope of the present embodiment. In FIG. 4, a specific arrangement of the light-beam splitting element is shown.

As shown in FIG. 4, the light-beam splitting element BS has the surface of incidence Sin and the surface of emergence Sout. The surface of incidence Sin includes a first surface of incidence Sin1 on which the first light ray LB1 is incident and a second surface of incidence Sin2 on which the second light ray LB2 is incident. The first surface of incidence Sin1 and the second surface of incidence Sin2 are plane-symmetric with respect to a plane including the optical axis AX.

Both of a normal of the first surface of incidence Sin1 and a normal of the second surface of incidence Sin2 intersect the optical axis AX. The first surface of incidence Sin1 and the second surface of incidence Sin2 have a shape such that a distance from the optical axis AX increases toward the object side from a point of intersection with the optical axis AX.

The surface of emergence Sout includes a first surface of emergence Sout1 on which the first light ray LB1 emerges and a second surface of emergence Sout2 on which the second light ray LB2 emerges. The first surface of emergence Sout1 and the second surface of emergence Sout2 are plane-symmetric with respect to a plane including the optical axis AX.

Both of a normal of the first surface of emergence Sout1 and a normal of the second surface of emergence Sout2 intersect the optical axis AX. The first surface of emergence Sout1 and the second surface of emergence Sout2 have a shape such that a distance from the optical axis AX increases toward the object side from a point of intersection with the optical axis AX.

In the stereoscopic-vision endoscope of the present embodiment, it is preferable that the following conditional expression (7) be satisfied:

$$0.05 \leq Divs/Ds \leq 0.7 \quad (7)$$

where,

Divs denotes the distance between the point of incidence and the point of emergence, and Ds denotes a distance between the surface of incidence and the surface of emergence, and here the point of incidence is the point of intersection of the first light ray and the surface of incidence, the point of emergence is the point of intersection of the first light ray and the surface of emergence, the distance is the distance in the parallax direction, and the parallax direction is the direction orthogonal to both of the optical axis of the first optical path and the optical axis of the second optical path.

In a case of not satisfying conditional expression (7), the distance between the surface of incidence and the surface of emergence becomes excessively wide. In this case, the height of a light ray passing through the light-beam splitting element becomes high. Consequently, the light-beam splitting element becomes large in size.

Moreover, in a case of not satisfying conditional expression (7), the distance between the surface of incidence and the surface of emergence becomes excessively narrow. In this case, various differences occur between the two chief rays. Here, the description will be made by using the upper subordinate light ray LU and the lower subordinate light ray LL in FIG. 3.

In the second image IL2, with reference to the optical axis AX2, a direction away from the optical axis AX is let to be a plus direction and a direction of approaching closer to the optical axis AX is let to be a minus direction. The upper subordinate light ray LU reaches a point PI+ in the plus direction of the second image IL2, and the lower subordinate light ray LL reaches a point PI− in the minus direction of the second image IL2.

A distance from the optical axis AX2 up to the point PI+ and a distance from the optical axis AX2 up to the point PI− are equal. Accordingly, the image height at the point PI+ and the image height at the point PI− are same. However, an optical-path length of a light ray reaching the point PI+ (hereinafter, referred to as 'light ray PI+') and an optical-path length of a light ray reaching the point PI− (hereinafter, referred to as 'light ray PI−') differ.

Consequently, a difference in an angle of incidence on the light-beam splitting element becomes large between the light ray PI+ and the light ray PI−. Similar is true for a difference in an angle of emergence from the light-beam splitting element. Moreover, the transmittance also varies for the light ray PI+ and the light ray PI−. Although the description has been made by using the subordinate light rays, similar is true for the chief ray.

As mentioned above, the optical-path length of the light ray PI+ and the optical-path length of the light ray PI− differ. With the image height becoming high, the difference in the optical-path length of the light ray PI+ and the optical-path length of the light ray PI− becomes large. Accordingly, with the image height becoming high, a difference in an amount of aberration at the point PI+ and an amount of aberration at the point PI− becomes large.

By making so as not to exceed an upper limit value of conditional expression (7), it is possible to prevent a difference in the optical paths of two off-axis light rays that form an image on a periphery of the image pickup element, such as the light ray PI+ and the light ray PI− from becoming large. As a result, it is possible to suppress the occurrence of the asymmetric aberration.

By making so as not to fall below a lower limit value of conditional expression (7), it is possible to prevent the height of a light ray passing through the light-beam splitting element from becoming excessively high. As a result, it is possible to prevent the light-beam splitting element from becoming large.

In the stereoscopic-vision endoscope of the present embodiment, it is preferable that the following conditional expression (8) be satisfied:

$$0.85 \leq Divax/(Ds/\mathrm{COS}\,\Theta \times \mathrm{SIN}(\theta-\Theta)) \leq 1.15 \quad (8)$$

where, $\theta = \mathrm{A\,SIN}\,((1/nBS) \times \mathrm{SIN}\,\theta)$,

Divax denotes a distance between the optical axis of the common optical path and the optical axis of the first optical path, Ds denotes the distance between the surface of incidence and the surface of emergence, θ denotes an angle made by a surface orthogonal to the optical axis of the common optical path and the surface of incidence, nBS denotes a refractive index of the light-beam splitting element for a d-line, the point of incidence is the point of intersection of the first light ray and the surface of incidence, the point of emergence is the point of intersection of the first light ray and the surface of emergence, the distance is the distance in the parallax direction, and the parallax direction is the direction orthogonal to both of the optical axis of the first optical path and the optical axis of the second optical path.

As shown in FIG. 4, Divax is a distance between the optical axis AX and the optical axis AX1. However, Divax may be a distance between the optical axis AX and the optical axis AX2.

By making so as not to exceed an upper limit value of conditional expression (8) or so as not to fall below a lower limit value of conditional expression (8), it is possible to suppress the occurrence of the decentering aberration due to the second lens unit.

It is possible to make the distance between the optical axis of the common optical path and the optical axis of the first optical path 1.41 mm for example. Moreover, it is possible to make the distance between the optical axis of the common optical path and the optical axis of the first optical path 1.6 mm for example. In this case, it is possible to secure largely the distance between the first optical path and the second optical path. At this time, a value in conditional expression becomes 1.14.

In the stereoscopic-vision endoscope of the present embodiment, it is preferable that the following conditional expression (9) be satisfied:

$$0.6 \leq \Phi RL\ \max/Ymid\text{img} \leq 3.5 \quad (9)$$

Where,

ΦRLmax denotes the maximum lens diameter of the relay optical system, and

Ymidimg denotes the maximum image height of the intermediate image.

Conditional expression (9) is a conditional expression related to the relay optical system. In the optical system of the stereoscopic-vision endoscope, when a barrel distortion occurs largely, it becomes difficult to achieve a high resolution performance in a periphery of an image. Therefore, it is necessary to make small the occurrence of the barrel distortion.

By making so as not to exceed an upper limit value of conditional expression (9), it is possible to suppress a distortion in particular, to be small, while maintaining a diameter and an angle of view desired for the stereoscopic-vision endoscope.

By making so as not to fall below a lower limit value of conditional expression (9), it is possible to suppress vignetting in an off-axis subordinate light ray. By the vignetting of the light ray being suppressed, it is possible to have a favorable resolution from a structure having a low-frequency component up to a structure having a high-frequency component, even in the periphery of the image.

In the stereoscopic-vision endoscope of the present embodiment, it is preferable that the following conditional expression (10) be satisfied:

$$0.6 \leq D2b/FLG1 \leq 2.5 \quad (10)$$

where,

D2b denotes a distance on the optical axis of the common optical path, between a position of a principal point on the image side of the first lens unit and the light-beam splitting element, and FLG1 denotes a focal length of the first lens unit.

By making so as not to exceed an upper limit value of conditional expression (10) or so as not to fall below a lower limit value of conditional expression (10), it is possible to suppress the vignetting in the off-axis subordinate light ray to be small. By the vignetting of the light ray being suppressed, it becomes insusceptible to diffraction even in the periphery of the image. Consequently, it is possible to achieve the favorable resolution performance even in the periphery of the image. In other words, it is possible to have a favorable resolution from the structure having the low-frequency component up to the structure having the high-frequency component.

In the stereoscopic-vision endoscope of the present embodiment, it is preferable that the following conditional expression (11) be satisfied:

$$0.2 \leq Ymid\text{img}/PBS\text{in} \leq 1.2 \quad (11)$$

where,

Ymidimg denotes the maximum image height of the intermediate image, and

PBSin denotes a height of an effective light ray incident on the light-beam splitting element.

By making so as not to exceed an upper limit value of conditional expression (11) or so as not to fall below a lower limit value of conditional expression (11), it is possible to suppress the vignetting in the off-axis subordinate light ray to be small. By the vignetting of the light ray being suppressed, it becomes insusceptible to the diffraction even in the periphery of the image. Consequently, it is possible to achieve the favorable resolution performance even in the periphery of the image. In other words, it is possible to have the favorable resolution from the structure having the low-frequency component up to the structure having the high-frequency component.

In the stereoscopic-vision endoscope of the present embodiment, it is preferable that the following conditional expression (12) be satisfied:

$$0.01 \leq Ymid\text{img}/FLG1 \leq 0.2 \quad (12)$$

where,

Ymidimg denotes the maximum image height of the intermediate image, and

FLG1 denotes the focal length of the first lens unit.

By satisfying conditional expression (12), it is possible to make small an angle of inclination of the chief ray due to the first lens unit. Accordingly, it is possible to suppress the occurrence of the asymmetric aberration in the plus direction and the minus direction.

By making so as not to exceed an upper limit value of conditional expression (12) or so as not to fall below a lower limit value of conditional expression (12), it is possible to suppress the decentering aberration which occurs due to a difference in the optical-path length of an upper and lower off-axis light rays. The difference in the optical-path length, for instance, is a difference in the optical-path length of the upper subordinate light ray LU and the optical-path length of the lower subordinate light ray LL.

In the stereoscopic-vision endoscope of the present embodiment, it is preferable that a predetermined pupil be a pupil that is formed at a position nearest to the intermediate image, on the object side of the intermediate image, and the light-beam splitting element be disposed at a position conjugate with the predetermined pupil.

By making such arrangement, it is possible to suppress the decentering aberration which occurs due to the difference in the optical-path length of the upper and lower off-axis light rays.

In the stereoscopic-vision endoscope of the present embodiment, it is preferable that the aperture stop be disposed on the image side of the intermediate image, and a shape of an opening portion of the aperture stop be a circular shape.

By making the aperture stop to be a circular stop, it is possible to make an axial light ray pass through an area near a lens center, while securing an adequate brightness. Consequently, it is possible to secure a state in which a spherical aberration is corrected favorably, particularly.

Figure 5A:
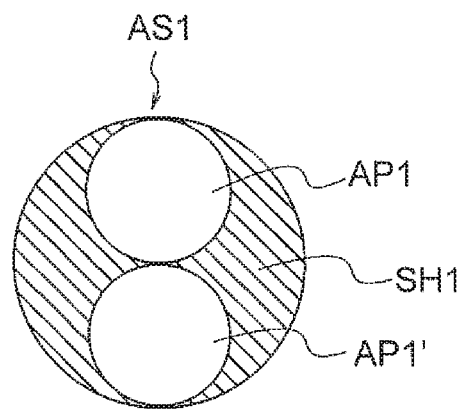
FIG. 5A, FIG. 5B, and FIG. 5C are diagrams showing aperture stops.
Figure 5B:
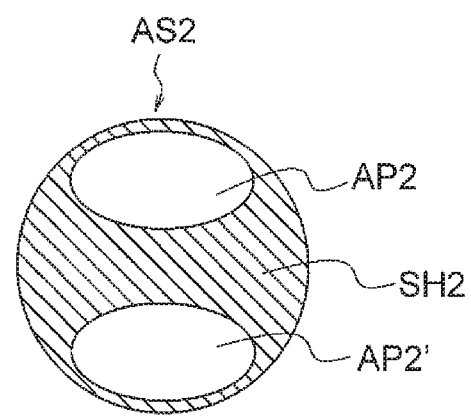
Figure 5C:
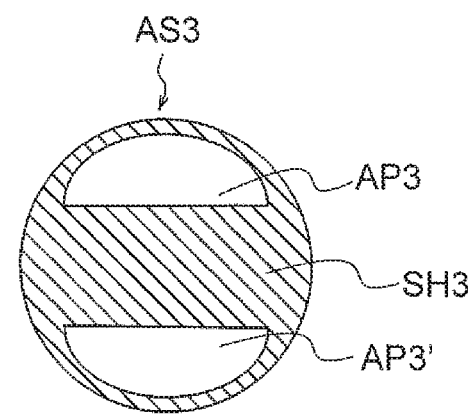

FIG. 5A, FIG. 5B, and FIG. 5C are diagrams showing aperture stops. FIG. 5A shows an aperture stop having a circular-shaped opening portion. An aperture stop AS1 has an opening portion AP1, an opening portion AP1', and alight-shielding portion SH1. Both a shape of the opening portion AP1 and a shape of the opening portion AP1' are circular. The opening portion AS1 is provided to be positioned in the first optical path OP1, and the opening portion AP1' is provided to be positioned in the second optical path OP2.

The light-shielding portion SH1 is an opaque member such as a metal plate. The opening portion AP1 and the opening portion AP1' are openings (holes) formed in the metal plate.

The light-shielding member SH1, the opening portion AP1, and the opening portion AP1' may have been formed of a transparent member such as a glass plate or a resin plate. The light-shielding member SH1 is formed by applying a light-shielding paint to a glass plate. Whereas, the opening portion AP1 and the opening portion AP1' have nothing applied thereto. Accordingly, the opening portion AP1 and the opening portion AP1' are glass plates per se.

In the stereoscopic-vision endoscope of the present embodiment, it is preferable that the aperture stop be disposed on the image side of the intermediate image, and a shape of an opening portion of the aperture stop be a shape having different lengths in two directions that are orthogonal, and one of the two directions be the parallax direction and the other direction be a direction orthogonal to the parallax direction.

By making such arrangement, it is possible to achieve both of securing an appropriate parallax and securing appropriately an area of the opening portion. Consequently, as compared to a case in which the shape of the opening portion is circular, it is possible to suppress a degradation of resolution performance due to diffraction while securing the parallax adequately.

FIG. 5B and FIG. 5C show aperture stops having a noncircular-shaped opening portion. An aperture stop AS2, as shown in FIG. 5B, has an opening portion AP2, an opening portion AP2', and a light-shielding portion SH2. Both a shape of the opening AP2 and a shape of the opening portion AP2' are elliptical.

An aperture stop AS3, as shown in FIG. 5C, has an opening portion AP3, an opening portion AP3', and a light-shielding portion SH3. Both a shape of the opening portion AP3 and a shape of the opening portion AP3' are substantially semicircular.

It is preferable that a length of the opening portion in the parallax direction be longer than a length of the opening portion in a direction orthogonal to the parallax direction.

It is preferable that a distance between an opening portion positioned in the first optical path and an opening portion positioned in the second optical path be as long as possible. By making such arrangement, it is possible to secure the parallax adequately.

It is preferable that a shape of the opening portion positioned in the first optical path and a shape of the opening portion positioned in the second optical path be identical. By making such arrangement, it is possible to make blurring in the first image and blurring in the second image identical.

In the aperture stop AS1, the aperture stop AS2, and the aperture stop AS3, two opening portions are provided in one member. However, two opening portions may be provided in separate members.

In the stereoscopic-vision endoscope of the present embodiment, it is preferable that the aperture stop be disposed on the image side of the intermediate image, and the following conditional expression (13) be satisfied:

$$0 < Lss/FLG1 \leq 0.8 \quad (13)$$

where,

Lss denotes a distance on the optical axis of the common optical path, between the surface of incidence and the aperture stop, and FLG1 denotes the focal length of the first lens unit.

By making so as not to exceed an upper limit value of conditional expression (13) or so as not to fall below a lower limit value of conditional expression (13), it is possible to suppress the vignetting in the off-axis subordinate light ray to be small. By the vignetting of a light ray being suppressed, it becomes insusceptible to the diffraction even in the periphery of the image. Consequently, it is possible to achieve the favorable resolution performance even in the periphery of the image, or in other words, it is possible to have the favorable resolution from the structure having the low-frequency component up to the structure having the high-frequency component.

In the stereoscopic-vision endoscope of the present embodiment, it is preferable that the following conditional expression (14) be satisfied:

$$0.01 \leq Yimg/FLG1 \leq 0.2 \quad (14)$$

where,

Yimg denotes the maximum image height, and

FLG1 denotes the focal length of the first lens unit.

By making so as not to exceed an upper limit value of conditional expression (14) or so as not to fall below a lower limit value of conditional expression (14), it is possible to suppress the vignetting in the off-axis subordinate light ray to be small. By the vignetting of a light ray being suppressed, it becomes insusceptible to the diffraction even in the periphery of the image. Consequently, it is possible to achieve the favorable resolution performance even in the periphery of the image, or in other words, it is possible to have the favorable resolution from the structure having the low-frequency component up to the structure having the high-frequency component.

In the stereoscopic-vision endoscope of the present embodiment, it is preferable that the following conditional expression (15) be satisfied:

$$0.01 \leq Yimg/FLG2 \leq 0.5 \quad (15)$$

where,

Yimg denotes the maximum image height, and

FLG2 denotes a focal length of the second lens unit.

By making so as not to exceed an upper limit value of conditional expression (15) or so as not to fall below a lower limit value of conditional expression (15), it is possible to secure a back focus appropriately.

In the stereoscopic-vision endoscope of the present embodiment, it is preferable that the first lens unit include a plurality of lenses, and at the time of focusing, at least some lenses of the plurality of lenses move along the optical axis of the common optical path.

By making such arrangement, it is possible to carry out focusing with the favorable resolution performance at any position between a near point and a far point.

In the stereoscopic-vision endoscope of the present embodiment, it is preferable that the second lens unit include a plurality of lenses, and at the time of focusing, at least some lenses of the plurality of lenses move along the optical axis of the first optical path or the optical axis of the second optical path.

By making such arrangement, it is possible to carry out focusing with the favorable resolution performance at any position of the object between the near point and the far point.

In the stereoscopic-vision endoscope of the present embodiment, it is preferable that the image pickup element have a first image pickup area which is positioned in the first optical path and a second image pickup area which is positioned in the second optical path, and a distance between a center of the first image pickup area and a center of the second image pickup area be longer than a distance between the optical axis of the first optical path and the optical axis of the second optical path.

The first image and the second image are captured by the image pickup element, and accordingly, an image of the first image and an image of the second image are acquired. The two images acquired are displayed on a monitor for example. It is possible to carry out stereoscopic-vision by the two images displayed on the monitor.

By making an arrangement as mentioned above, at the time of stereoscopic vision, it is easy to forma stereoscopic image at a position far from a position of the monitor, viewed from an observer. Consequently, it is possible to reduce fatigue accumulation of the observer at the time of stereoscopic vision.

With an arrangement in which the first light ray and the second light ray in the object space intersect at a position when the object distance is 60 mm, the first effective area and the second effective area are to be shifted by 10 μm in the parallax direction. By doing so, it is possible to shift the point of intersection of the left and right light rays to a position when the object distance is 30 mm. As a result, at the time of forming a stereoscopic image, it is possible to form an image of an object which is positioned at a close distance, at a distance far from the observer, while making an angle of view of the endoscope optical system large.

In the stereoscopic-vision endoscope of the present embodiment, it is preferable that a flare aperture which shields light rays other than an effective light ray, be positioned on the image side of the intermediate image.

By making such arrangement, it is possible to suppress an occurrence of a ghost. It is effective to dispose the flare aperture particularly on the object side or on the image side of the light-beam splitting element and on a side where an optical stop has not been disposed.

For each conditional expression, the lower limit value or the upper limit value may be changed as follows.

For conditional expression (1), it is preferable to let the lower limit value to be −0.05, and it is preferable to let the upper limit value to be 0.05.

For conditional expression (2), it is preferable to let the lower limit value to be −0.005, and it is preferable to let the upper limit value to be 0.005.

For conditional expression (3), it is preferable to let the lower limit value to be −0.005, and it is preferable to let the upper limit value to be 0.005.

For conditional expression (4), it is preferable to let the lower limit value to be 0.07 or 0.09, and it is preferable to let the upper limit value to be 1.5 or 1.3.

For conditional expression (5), it is preferable to let the lower limit value to be 0.8 or 0.9, and it is preferable to let the upper limit value to be 1.2 or 1.1.

For conditional expression (6), it is preferable to let the lower limit value to be 0.9 or 0.95, and it is preferable to let the upper limit value to be 1.1 or 1.05.

For conditional expression (7), it is preferable to let the lower limit value to be 0.08 or 0.1, and it is preferable to let the upper limit value to be 0.5 or 0.3.

For conditional expression (8), it is preferable to let the lower limit value to be 0.9 or 0.95, and it is preferable to let the upper limit value to be 1.1 or 1.05.

For conditional expression (9), it is preferable to let the lower limit value to be 0.8 or 1, and it is preferable to let the upper limit value to be 3.3 or 3.

For conditional expression (10), it is preferable to let the lower limit value to be 75 or 0.9, and it is preferable to let the upper limit value to be 2 or 1.7.

For conditional expression (11), it is preferable to let the lower limit value to be 0.3 or 0.4, and it is preferable to let the upper limit value to be 1.1 or 1.

For conditional expression (12), it is preferable to let the lower limit value to be 0.025 or 0.04, and it is preferable to let the upper limit value to be 0.17 or 0.15.

For conditional expression (13), it is preferable to let the lower limit value to be 0.1 or 0.2, and it is preferable to let the upper limit value to be 0.75 or 0.6.

For conditional expression (14), it is preferable to let the lower limit value to be 0.02 or 0.03, and it is preferable to let the upper limit value to be 0.15 or 0.1.

For conditional expression (15), it is preferable to let the lower limit value to be 0.03 or 0.05, and it is preferable to let the upper limit value to be 0.3 or 0.2.

Examples of optical systems for endoscope to be used in a stereoscopic-vision endoscope will be described below in detail by referring to the accompanying diagrams. However, the present invention is not restricted to the embodiments and the examples described below.

Figure 6:
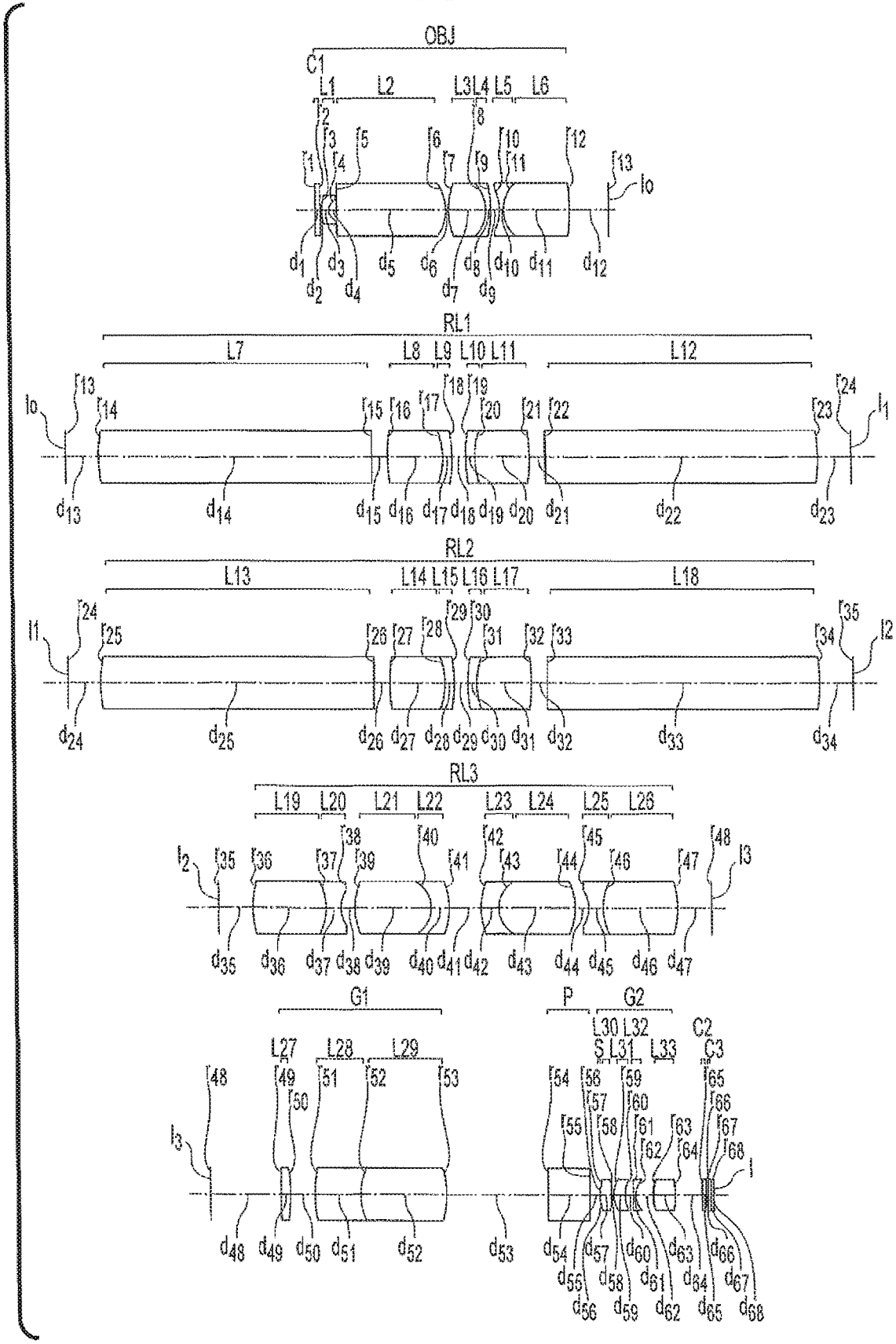
FIG. 6 is a lens cross-sectional view of an optical system for endoscope of an example 1.
Figure 10:
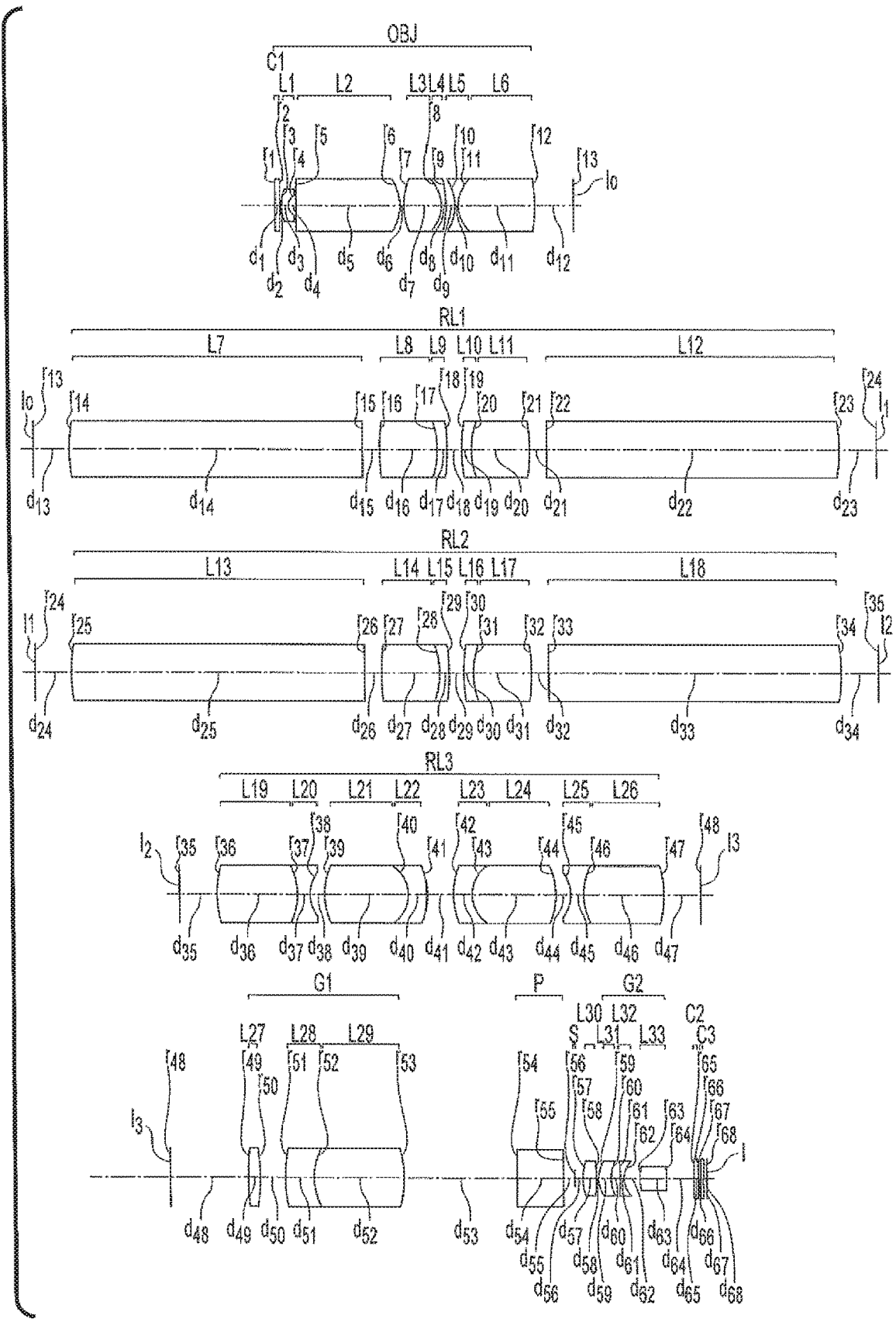
FIG. 10 is a lens cross-sectional view of an optical system for endoscope of an example 2.
Figure 12:
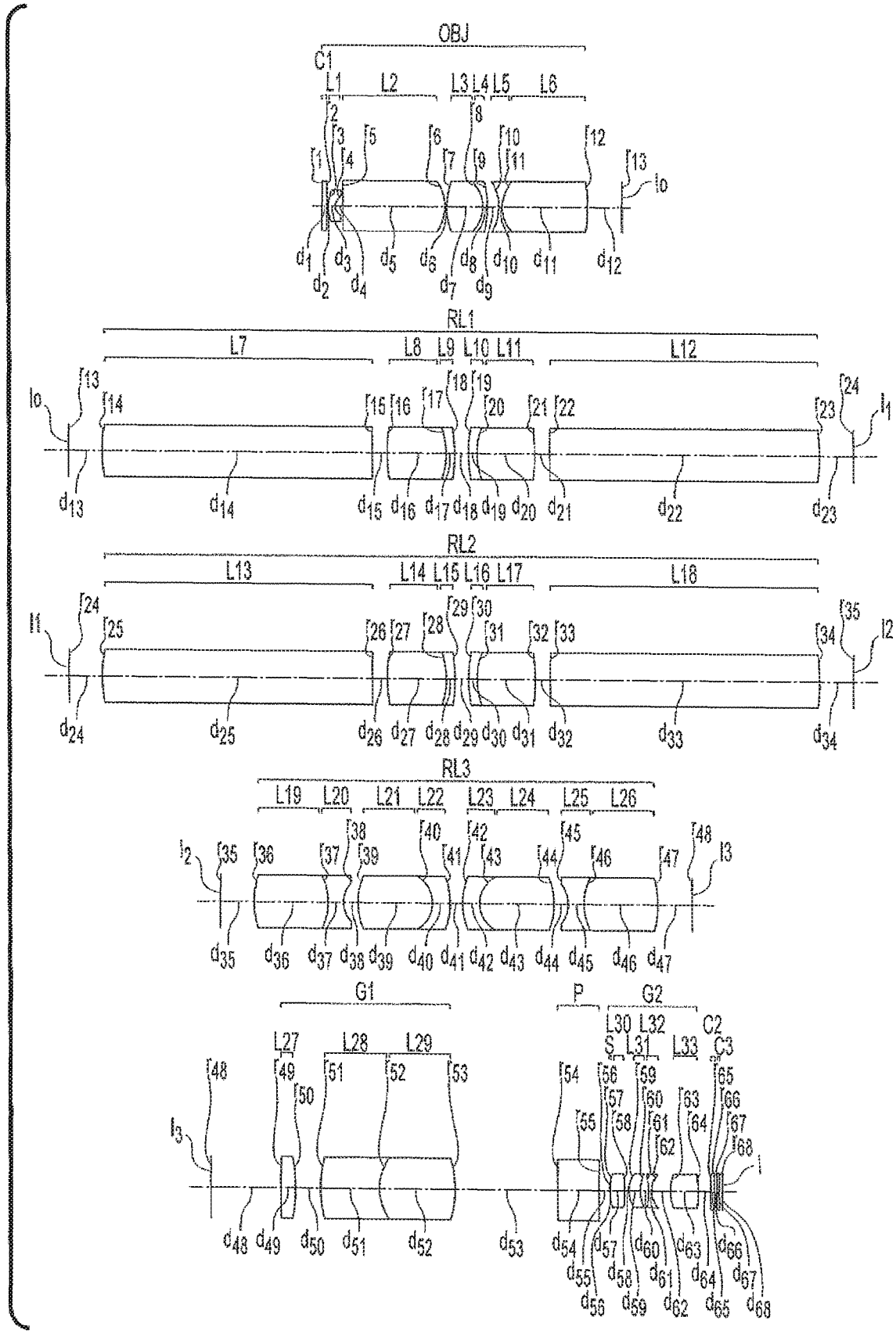
FIG. 12 is a lens cross-sectional view of an optical system for endoscope of an example 3.

Examples of an optical system for endoscope will be described below. FIG. 6, FIG. 10, and FIG. 12 are lens cross-sectional views of optical systems for endoscope of examples. These lens cross-sectional views are lens cross-sectional views in an X-Z plane. Here, the optical axis AX of the common optical path OP is let to be a Z-axis, an axis orthogonal to the Z-axis and parallel to the parallax direction is let to be a Y-axis, and an axis orthogonal to both the Z-axis and the Y-axis is let to be an X-axis.

Figure 7:
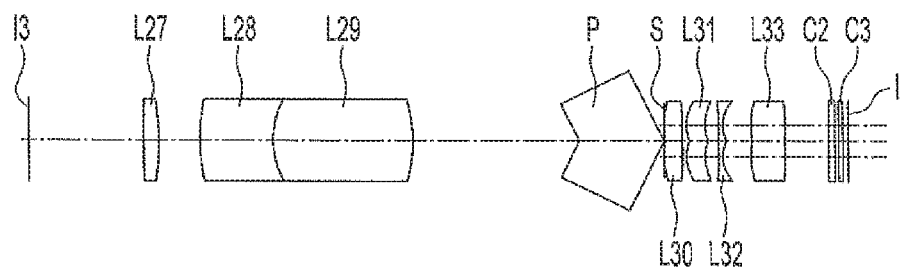
FIG. 7 is a lens cross-sectional view of a portion of the optical system for endoscope of the example 1.
Figure 11:
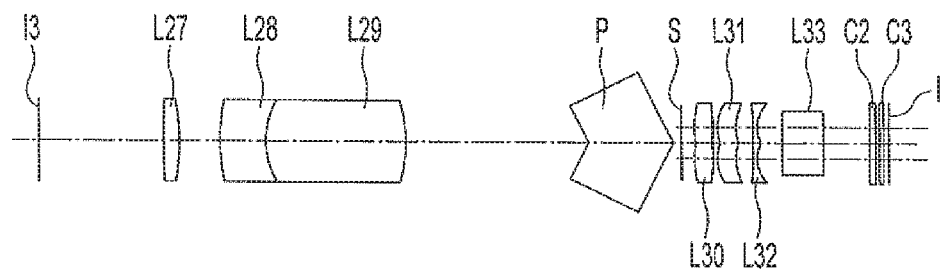
FIG. 11 is a lens cross-sectional view of a portion of the optical system for endoscope of the example 2.
Figure 13:
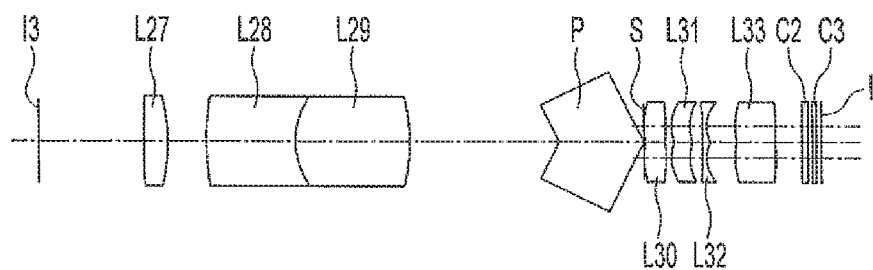
FIG. 13 is a lens cross-sectional view of a portion of the optical system for endoscope of the example 3.
Figure 15A:
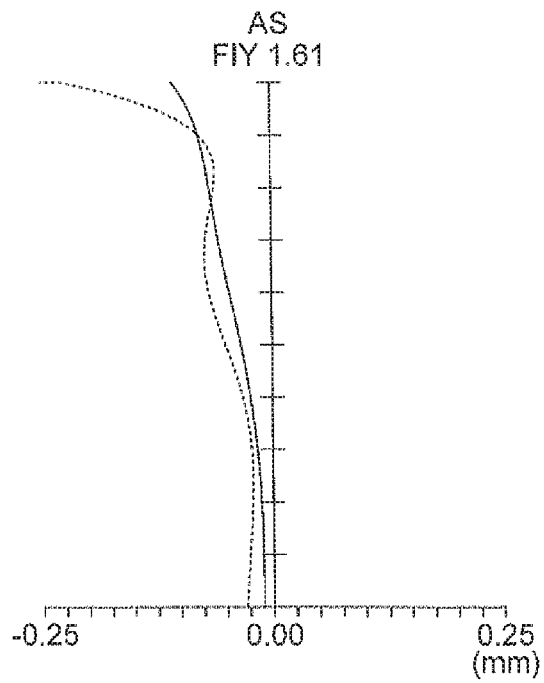
FIG. 15A, FIG. 15B, FIG. 15C, FIG. 15D, FIG. 15E, FIG. 15F, FIG. 15G, FIG. 15H, FIG. 15I, and FIG. 15J (hereinafter, FIG. 15A to FIG. 15J) are aberration diagrams of the optical system for endoscope of the example 1.
Figure 15B:
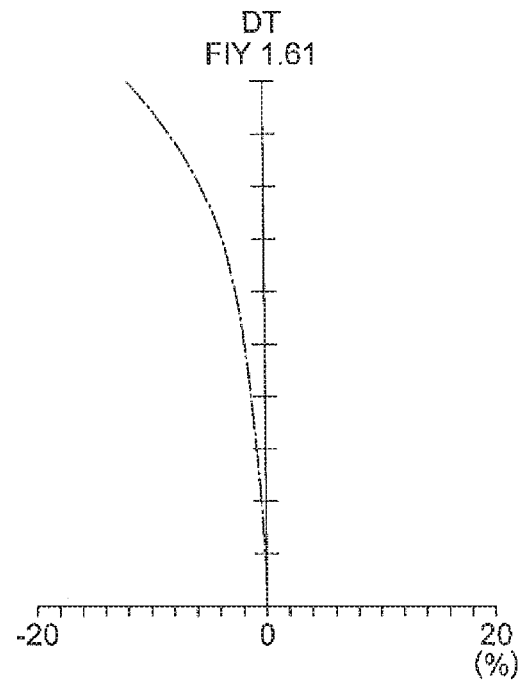
Figure 15C:
Figure 15D:
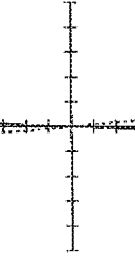
Figure 15E:
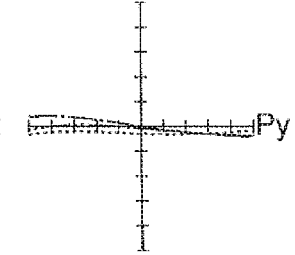
Figure 15F:
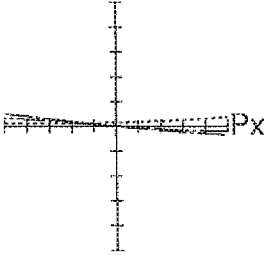
Figure 15G:
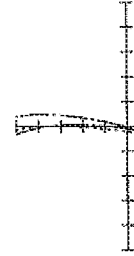
Figure 15H:
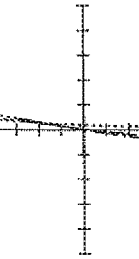
Figure 15I:
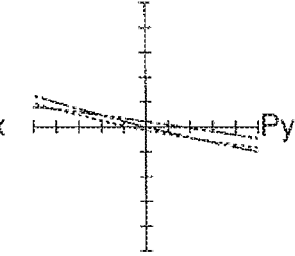
Figure 15J:
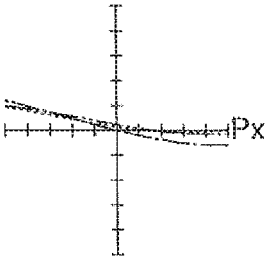
Figure 16A:
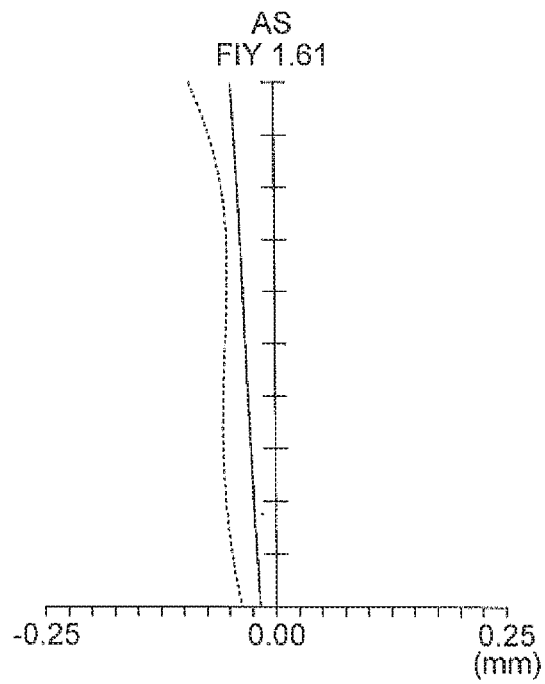
Figure 16B:
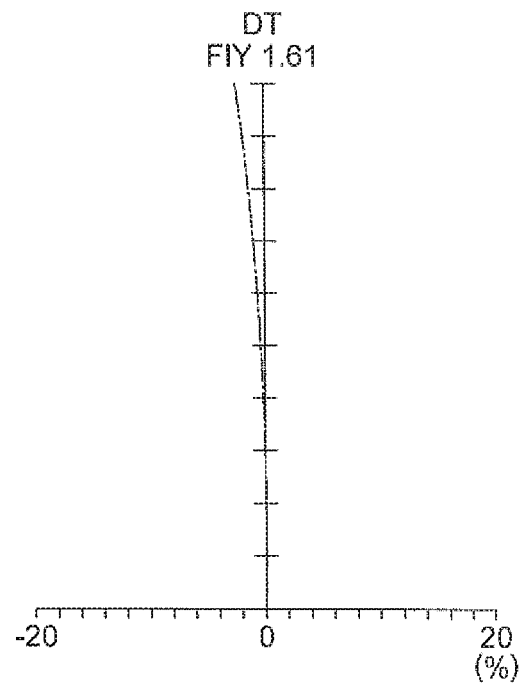
Figure 16B:
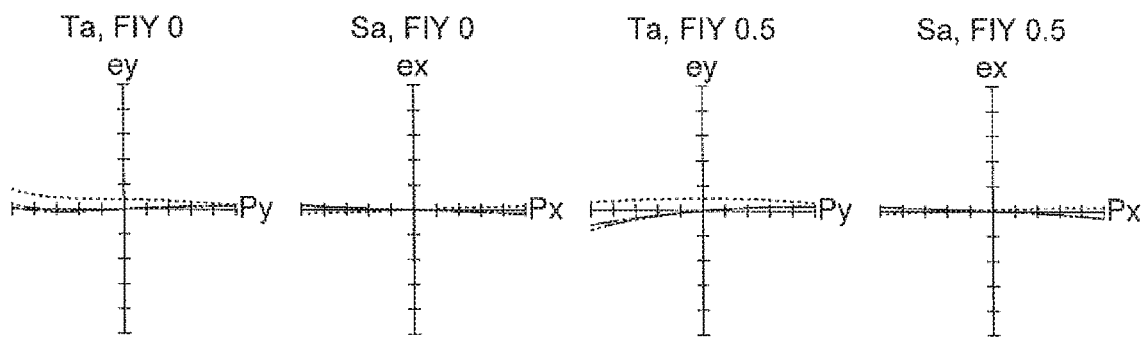
Figure 16B:
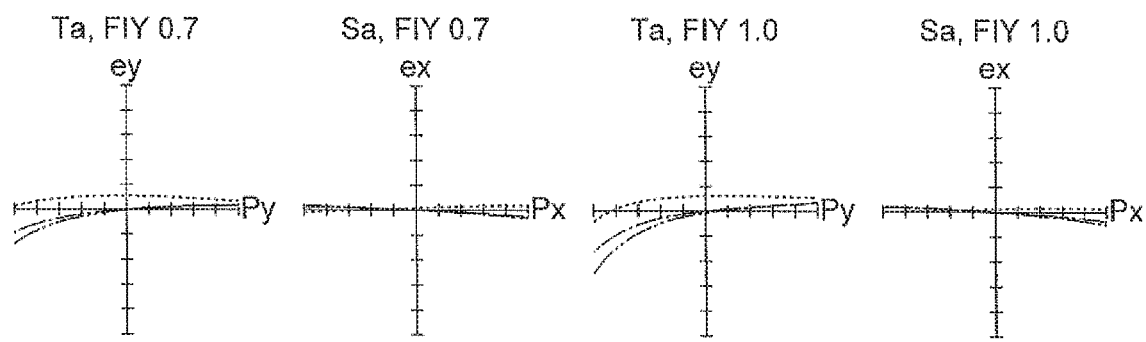
Figure 17A:
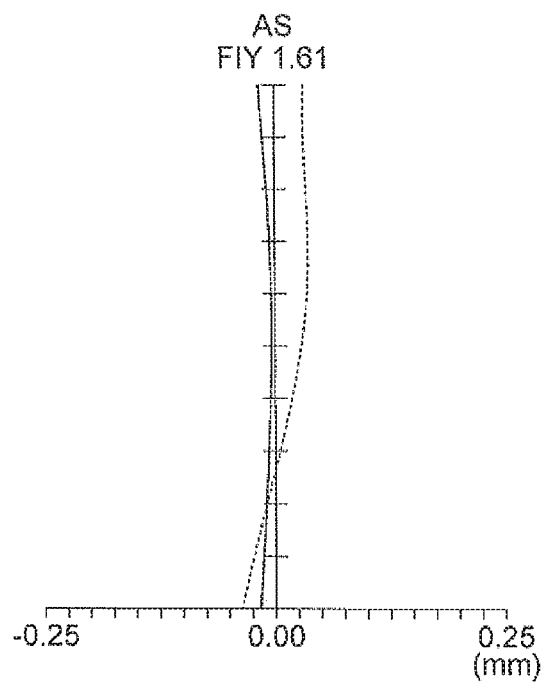
FIG. 17A, FIG. 17B, FIG. 17C, FIG. 17D, FIG. 17E, FIG. 17F, FIG. 17G, FIG. 17H, FIG. 17I, and FIG. 17J (hereinafter, FIG. 17A to FIG. 17J) are aberration diagrams of the optical system for endoscope of the example 2.
Figure 17B:
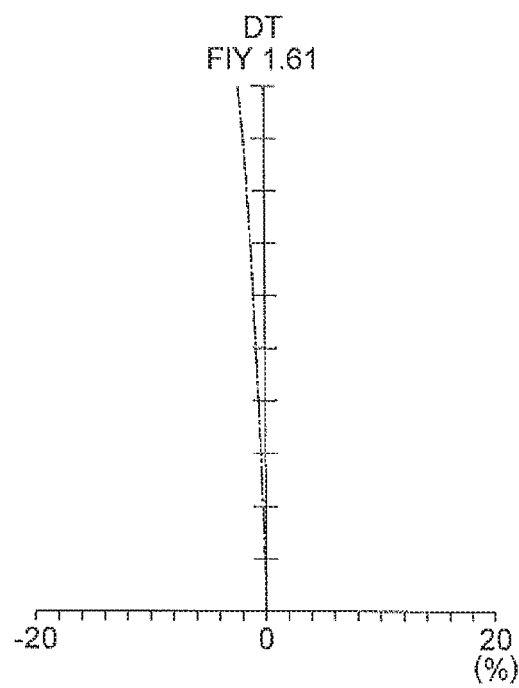
Figures 17C, 17D, 17E, 17F:
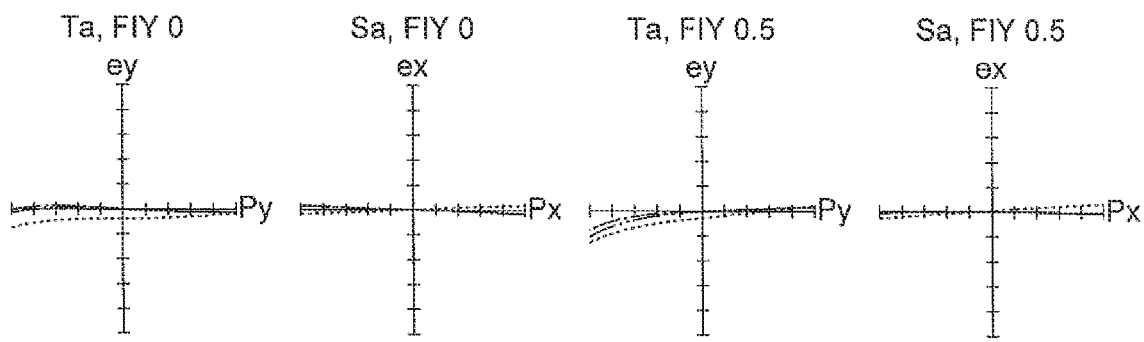
Figures 17G, 17H, 17I, 17J:
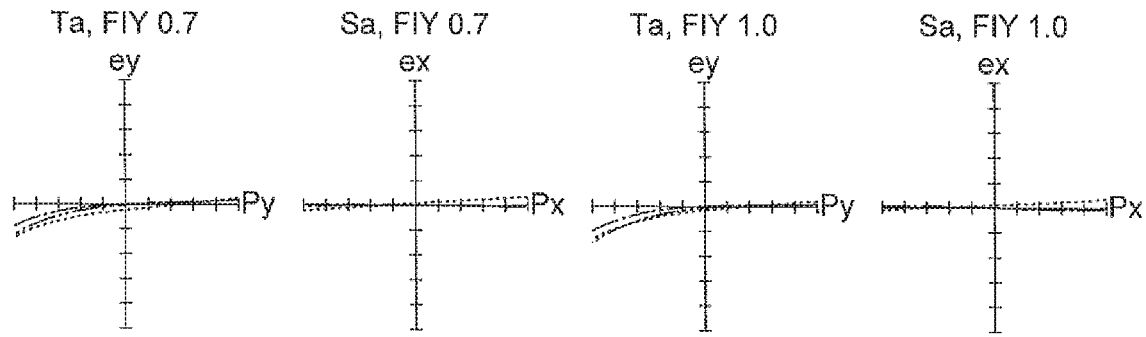

FIG. 7, FIG. 11, and FIG. 13 are lens cross-sectional views of a portion of the optical system for endoscope of examples. These lens cross-sectional views are lens cross-sectional views in a Y-Z plane. The lens cross-sectional view in FIG. 7 is a lens cross-sectional view of an optical system positioned on the image side of an intermediate image I3. Moreover, a cross-sectional surface in FIG. 7 is a cross-sectional surface orthogonal to a cross-sectional surface in FIG. 6.

Figure 8:
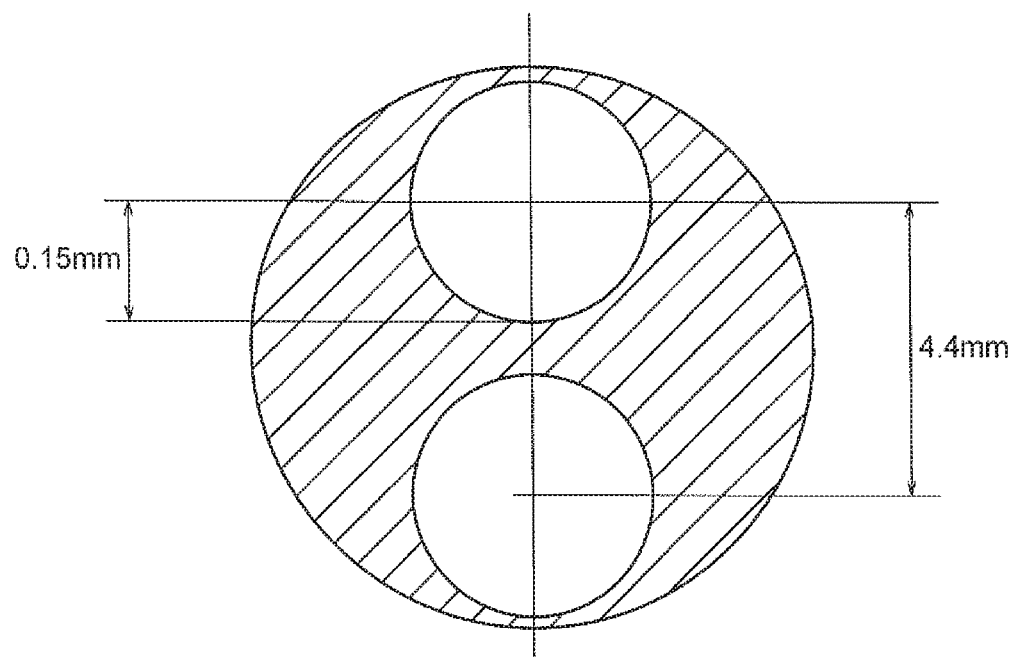
FIG. 8 is a diagram showing an aperture stop in the optical system for endoscope of the example 1.
Figure 9A:
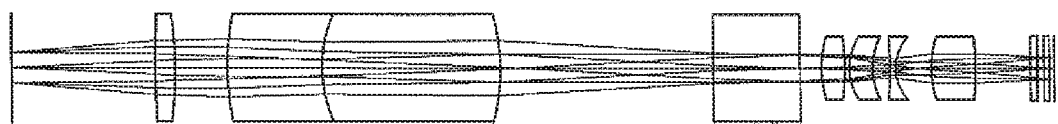
FIG. 9A and FIG. 9B are light-ray diagrams of the optical system for endoscope of the example 1.
Figure 9B:
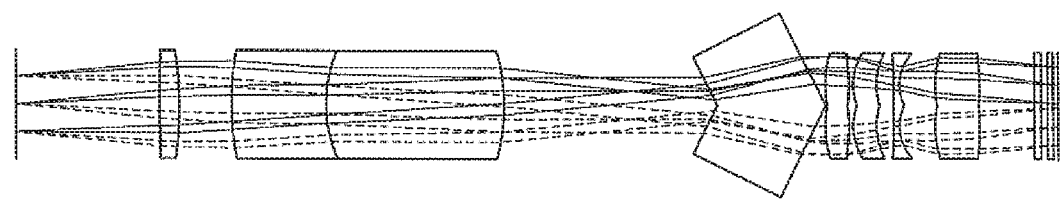

FIG. 8 is a diagram shown an aperture stop in an optical system for endoscope of an example 1. The aperture stop has two opening portions having a circular shape. FIG. 9A and FIG. 9B are light-ray diagrams of the optical system for endoscope of the example 1. FIG. 9A is a light-ray diagram in a cross-sectional surface same as in FIG. 6. FIG. 9B is a light-ray diagram in a cross-sectional surface same as in FIG. 7.

FIG. 14A to FIG. 14J, FIG. 15A to FIG. 15J, FIG. 16A to FIG. 16J, FIG. 17A to FIG. 17J, FIG. 18A to FIG. 18J, and FIG. 19A to FIG. 19J are aberration diagrams of the optical systems for endoscope of the examples.

FIG. 14A, FIG. 15A, FIG. 16A, FIG. 17A, FIG. 18A, and FIG. 19A show an astigmatism (AS).

FIG. 14B, FIG. 15B, FIG. 16B, FIG. 17B, FIG. 18B, and FIG. 19B show a distortion (DT).

FIG. 14C, FIG. 14D, FIG. 14E, FIG. 14F, FIG. 14G, FIG. 14H, FIG. 14I, FIG. 14J, FIG. 15C, FIG. 15D, FIG. 15E, FIG. 15F, FIG. 15G, FIG. 15H, FIG. 15I, FIG. 15J, FIG. 16C, FIG. 16D, FIG. 16E, FIG. 16F, FIG. 16G, FIG. 16H, FIG. 16I, FIG. 16J, FIG. 17C, FIG. 17D, FIG. 17E, FIG. 17F, FIG. 17G, FIG. 17H, FIG. 17I, FIG. 17J, FIG. 18C, FIG. 18D, FIG. 18E, FIG. 18F, FIG. 18G, FIG. 18H, FIG. 18I, FIG. 18J, FIG. 19C, FIG. 19D, FIG. 19E, FIG. 19F, FIG. 19G, FIG. 19H, FIG. 19I, and FIG. 19J show a transverse aberration.

In the transverse aberration, the maximum value of the horizontal axis is ±25 μm. A vertical axis is normalized by an entrance-pupil diameter. Ta denotes a tangential direction and Sa denotes a sagittal direction. Moreover, FIY 0 denotes an axial, FIY 0.5 denotes 0.5 times of the maximum image height, FIY 0.7 denotes 0.7 times of the maximum image height, and FIY 1.0 denotes 1.0 times of the maximum image height.

FIG. 14A to FIG. 14J, FIG. 16A to FIG. 16J, FIG. 18A to FIG. 18J, are aberration diagrams for an image on an upper-right side from the optical axis AX1 in the optical image IL1 shown in FIG. 2A. FIG. 15A to FIG. 15J, FIG. 17A to FIG. 17J, and FIG. 19A to FIG. 19J are aberration diagrams for an image on a lower-left side from the optical axis AX1 in the optical image IL1.

The optical system for endoscope of the example 1 includes in order from an object side, an objective optical system OBJ, an image relay unit, a first lens unit G1, a light-beam splitting element P, and a second lens unit G2. The image relay unit includes a first relay optical system RL1, a second relay optical system RL2, and a third relay optical system RL3.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image 12 is formed. The second relay image 12 is relayed by the third relay optical system RL3. Accordingly, a third relay image I3 is formed. The third relay image I3 is the intermediate image.

The first lens unit G1, the light-beam splitting element P, and the second lens unit G2 are disposed on an image side of the third relay image I3. An image I is formed by the first lens unit G1, the light-beam splitting element P, and the second lens unit G2.

The objective optical system OBJ includes in order from the object side, a negative meniscus lens L1 having a convex surface directed toward the object side, a planoconvex positive lens L2, a biconvex positive lens L3, a negative meniscus lens L4 having a convex surface directed toward the image side, a biconcave negative lens L5, and a biconvex positive lens L6. Here, the biconvex positive lens L3 and the negative meniscus lens L4 are cemented. The biconcave negative lens L5 and the biconvex positive lens L6 are cemented. A cover glass C1 is disposed on the object side of the negative meniscus lens L1.

The first relay optical system RL1 includes a planoconvex positive lens L7, a biconvex positive lens L8, a negative meniscus lens L9 having a convex surface directed toward the image side, a negative meniscus lens L10 having a convex surface directed toward the object side, a biconvex positive lens L11, and a planoconvex positive lens L12. Here, the biconvex positive lens L8 and the negative meniscus lens L9 are cemented. The negative meniscus lens L10 and the biconvex positive lens L11 are cemented.

The second relay optical system RL2 is an optical system identical to the first relay optical system RL1. The second relay optical system RL2 includes a planoconvex positive lens L13, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18. Here, the biconvex positive lens L14 and the negative meniscus lens L15 are cemented. The negative meniscus lens L16 and the biconvex positive lens L17 are cemented.

The third relay optical system RL3 includes a biconvex positive lens L19, a biconcave negative lens L20, a biconvex positive lens L21, a negative meniscus lens L22 having a convex surface directed toward the image side, a negative meniscus lens L23 having a convex surface directed toward the object side, a biconvex positive lens L24, a biconcave negative lens L25, and a biconvex positive lens L26. Here, the biconvex positive lens L19 and the biconcave negative lens L20 are cemented. The biconvex positive lens L21 and the negative meniscus lens L22 are cemented. The negative meniscus lens L23 and the biconvex positive lens L24 are cemented. The biconcave negative lens L25 and the biconvex positive lens L26 are cemented.

The first lens unit G1 includes a biconvex positive lens L27, a negative meniscus lens L28 having a convex surface directed toward the object side, and a biconvex positive lens L29. Here, the negative meniscus lens L28 and the biconvex positive lens L29 are cemented.

The light-beam splitting element P has a surface of incidence and a surface of emergence. The surface of incidence and the surface of emergence have a shape such that a distance from an optical axis increases toward the object side from a point of intersection with the optical axis.

The second lens unit G2 includes a biconvex positive lens L30, a positive meniscus lens L31 having a convex surface directed toward the object side, a biconcave negative lens L32, and a biconvex positive lens L33. A cover glass C2 and a cover glass C3 are disposed on the image side of the biconvex positive lens L33.

An optical system for endoscope of an example 2 includes in order from an object side, an objective optical system OBJ, an image relay unit, a first lens unit G1, a light-beam splitting element P, and a second lens unit G2. The image relay unit includes a first relay optical system RL1, a second relay optical system RL2, and a third relay optical system RL3.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image 12 is formed. The second relay image 12 is relayed by the third relay optical system RL3. Accordingly, a third relay image I3 is formed. The third relay image I3 is the intermediate image.

The first lens unit G1, the light-beam splitting element P, and the second lens unit G2 are disposed on an image side of the third relay image I3. An image I is formed by the first lens unit G1, the light-beam splitting element P, and the second lens unit G2.

The objective optical system OBJ includes in order from the object side, a negative meniscus lens L1 having a convex surface directed toward the object side, a planoconvex positive lens L2, a biconvex positive lens L3, a negative meniscus lens L4 having a convex surface directed toward the image side, a biconcave negative lens L5, and a biconvex positive lens L6. Here, the biconvex positive lens L3 and the negative meniscus lens L4 are cemented. The biconcave negative lens L5 and the biconvex positive lens L6 are cemented. A cover glass C1 is disposed on the object side of the negative meniscus lens L1.

The first relay optical system RL1 includes a planoconvex positive lens L7, a biconvex positive lens L8, a negative meniscus lens L9 having a convex surface directed toward the image side, a negative meniscus lens L10 having a convex surface directed toward the object side, a biconvex positive lens L11, and a planoconvex positive lens L12. Here, the biconvex positive lens L8 and the negative meniscus lens L9 are cemented. The negative meniscus lens L10 and the biconvex positive lens L11 are cemented.

The second relay optical system RL2 is an optical system identical to the first relay optical system RL1. The second relay optical system RL2 includes a planoconvex positive lens L13, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18. Here, the biconvex positive lens L14 and the negative meniscus lens L15 are cemented. The negative meniscus lens L16 and the biconvex positive lens L17 are cemented.

The third relay optical system RL3 includes a biconvex positive lens L19, a biconcave negative lens L20, a biconvex positive lens L21, a negative meniscus lens L22 having a convex surface directed toward the image side, a negative meniscus lens L23 having a convex surface directed toward the object side, a biconvex positive lens L24, a biconcave negative lens L25, and a biconvex positive lens L26. Here, the biconvex positive lens L19 and the biconcave negative lens L20 are cemented. The biconvex positive lens L21 and the negative meniscus lens L22 are cemented. The negative meniscus lens L23 and the biconvex positive lens L24 are cemented. The biconcave negative lens L25 and the biconvex positive lens L26 are cemented.

The first lens unit G1 includes a biconvex positive lens L27, a negative meniscus lens L28 having a convex surface directed toward the object side, and a biconvex positive lens L29. Here, the negative meniscus lens L28 and the biconvex positive lens L29 are cemented.

The light-beam splitting element P has a surface of incidence and a surface of emergence. The surface of incidence and the surface of emergence have a shape such that a distance from an optical axis increases toward the object side from a point of intersection with the optical axis.

The second lens unit G2 includes a biconvex positive lens L30, a positive meniscus lens L31 having a convex surface directed toward the object side, a biconcave negative lens L32, and a biconvex positive lens L33. A cover glass C2 and a cover glass C3 are disposed on the image side of the biconvex positive lens L33.

An optical system for endoscope of an example 3 includes in order from an object side, an objective optical system OBJ, an image relay unit, a first lens unit G1, a light-beam splitting element P, and a second lens unit G2. The image relay unit includes a first relay optical system RL1, a second relay optical system RL2, and a third relay optical system RL3.

A primary image Io is formed by the objective optical system OBJ. The primary image Io is relayed by the first relay optical system RL1. Accordingly, a first relay image I1 is formed. The first relay image I1 is relayed by the second relay optical system RL2. Accordingly, a second relay image I2 is formed. The second relay image I2 is relayed by the third relay optical system RL3. Accordingly, a third relay image I3 is formed. The third relay image I3 is the intermediate image.

The first lens unit G1, the light-beam splitting element P, and the second lens unit G2 are disposed on an image side of the third relay image I3. An image I is formed by the first lens unit G1, the light-beam splitting element P, and the second lens unit G2.

The objective optical system OBJ includes in order from the object side, a negative meniscus lens L1 having a convex surface directed toward the object side, a planoconvex positive lens L2, a biconvex positive lens L3, a negative meniscus lens L4 having a convex surface directed toward the image side, a biconcave negative lens L5, and a biconvex positive lens L6. Here, the biconvex positive lens L3 and the negative meniscus lens L4 are cemented. The biconcave negative lens L5 and the biconvex positive lens L6 are cemented. A cover glass C1 is disposed on the object side of the negative meniscus lens L1.

The first relay optical system RL1 includes a planoconvex positive lens L7, a biconvex positive lens L8, a negative meniscus lens L9 having a convex surface directed toward the image side, a negative meniscus lens L10 having a convex surface directed toward the object side, a biconvex positive lens L11, and a planoconvex positive lens L12. Here, the biconvex positive lens L8 and the negative meniscus lens L9 are cemented. The negative meniscus lens L10 and the biconvex positive lens L11 are cemented.

The second relay optical system. RL2 is an optical system identical to the first relay optical system RL1. The second relay optical system RL2 includes a planoconvex positive lens L13, a biconvex positive lens L14, a negative meniscus lens L15 having a convex surface directed toward the image side, a negative meniscus lens L16 having a convex surface directed toward the object side, a biconvex positive lens L17, and a planoconvex positive lens L18. Here, the biconvex positive lens L14 and the negative meniscus lens L15 are cemented. The negative meniscus lens L16 and the biconvex positive lens L17 are cemented.

The third relay optical system RL3 includes a biconvex positive lens L19, a biconcave negative lens L20, a biconvex positive lens L21, a negative meniscus lens L22 having a convex surface directed toward the image side, a negative meniscus lens L23 having a convex surface directed toward the object side, a biconvex positive lens L24, a biconcave negative lens L25, and a biconvex positive lens L26. Here, the biconvex positive lens L19 and the biconcave negative lens L20 are cemented. The biconvex positive lens L21 and the negative meniscus lens L22 are cemented. The negative meniscus lens L23 and the biconvex positive lens L24 are cemented. The biconcave negative lens L25 and the biconvex positive lens L26 are cemented.

The first lens unit G1 includes a biconvex positive lens L27, a negative meniscus lens L28 having a convex surface directed toward the object side, and a biconvex positive lens L29. Here, the negative meniscus lens L28 and the biconvex positive lens L29 are cemented.

The light-beam splitting element P has a surface of incidence and a surface of emergence. The surface of incidence and the surface of emergence have a shape such that a distance from an optical axis increases toward the object side from a point of intersection with the optical axis.

The second lens unit G2 includes a biconvex positive lens L30, a positive meniscus lens L31 having a convex surface directed toward the object side, a biconcave negative lens L32, and a biconvex positive lens L33. A cover glass C2 and a cover glass C3 are disposed on the image side of the biconvex positive lens L33.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, and *denotes an aspherical surface.

In various numerical data, f denotes a focal length of the endoscope optical system, FIY denotes the maximum image height, and FNO denotes an F-number. Moreover, in aspect-ratio data, FIY 0.5 denotes 0.5 times of the maximum image height, FIY 0.7 denotes 0.7 times of the maximum image height, and FIY 1.0 denotes 1.0 times of the maximum image height.

A shape of an aspherical surface is defined by the following expression where the direction of the optical axis is represented by z, the direction orthogonal to the optical axis is represented by y, a conical coefficient is represented by K, aspherical surface coefficients are represented by A4, A6, A8, A10, A12 . . . .

$$Z=(y^2/r)/[1+\{1-(1+k)(y/r)^2\}^{1/2}]+A4y^4+A6y^6+A8y^8+A10y^{10}+A12y^{12}+\ldots$$

Further, in the aspherical surface coefficients, 'E-n' (where, n is an integral number) indicates '$10^{-n}$'. Moreover, these symbols are commonly used in the following numerical data for each example.

Moreover, in decentering data, a decentering amount is denoted by X, Y, and Z, and an angle of inclination is denoted by α, β, and γ. Here, X denotes a decentering amount in an X-axis direction, Y denotes a decentering amount in a Y-axis direction, and Z denotes a decentering amount in a Z-axis direction. Moreover, α denotes an angle of inclination with respect to the X-axis, β denotes an angle of inclination with respect to the Y-axis, and γ denotes an angle of inclination with respect to the Z-axis.

For instance, in a numerical example 1, a value of β on a 54$^{th}$ surface in the first optical path is a negative value. This indicates that the 54$^{th}$ surface in the first optical path is in a state of a plane rotated in a counterclockwise direction from the Y-axis.

Example 1

Unit mm

Surface data

| Surface no. | r | d | nd | vd |
|---|---|---|---|---|
| Object plane | ∞ | 45.000 | | |
| 1 | ∞ | 0.808 | 1.769 | 64.15 |
| 2 | ∞ | 0.231 | | |
| 3* | 13.058 | 1.212 | 1.806 | 40.93 |
| 4* | 1.929 | 1.385 | | |
| 5 | ∞ | 18.316 | 1.806 | 40.93 |
| 6 | −8.083 | 0.682 | | |
| 7 | 11.817 | 6.555 | 1.497 | 81.55 |
| 8 | −6.399 | 0.808 | 1.847 | 23.78 |
| 9 | −20.664 | 1.635 | | |
| 10 | −7.942 | 0.577 | 1.648 | 33.79 |
| 11 | 6.189 | 13.458 | 1.883 | 40.77 |
| 12 | −29.965 | 6.704 | | |
| 13 | ∞ | 5.769 | | |
| 14 | 27.433 | 46.190 | 1.516 | 64.14 |
| 15 | ∞ | 2.651 | | |
| 16 | 31.907 | 9.265 | 1.497 | 81.55 |
| 17 | −12.967 | 1.529 | 1.755 | 52.32 |
| 18 | −26.692 | 2.308 | | |
| 19 | 26.692 | 1.529 | 1.755 | 52.32 |
| 20 | 12.967 | 9.265 | 1.497 | 81.55 |
| 21 | −31.907 | 2.651 | | |
| 22 | ∞ | 46.190 | 1.516 | 64.14 |
| 23 | −27.433 | 5.769 | | |
| 24 | ∞ | 5.769 | | |
| 25 | 27.433 | 46.190 | 1.516 | 64.14 |
| 26 | ∞ | 2.651 | | |
| 27 | 31.907 | 9.265 | 1.497 | 81.55 |
| 28 | −12.967 | 1.529 | 1.755 | 52.32 |
| 29 | −26.692 | 2.308 | | |
| 30 | 26.692 | 1.529 | 1.755 | 52.32 |
| 31 | 12.967 | 9.265 | 1.497 | 81.55 |
| 32 | −31.907 | 2.651 | | |
| 33 | ∞ | 46.190 | 1.516 | 64.14 |
| 34 | −27.433 | 5.769 | | |
| 35 | ∞ | 5.769 | | |
| 36 | 15.852 | 12.576 | 1.883 | 40.77 |
| 37 | −9.714 | 2.476 | 1.673 | 38.15 |
| 38 | 5.517 | 2.349 | | |
| 39 | 10.720 | 13.106 | 1.497 | 81.55 |
| 40 | −5.171 | 3.011 | 1.516 | 64.14 |
| 41 | −11.856 | 5.481 | | |
| 42 | 11.856 | 3.011 | 1.516 | 64.14 |
| 43 | 5.171 | 13.106 | 1.497 | 81.55 |
| 44 | −10.720 | 2.349 | | |
| 45 | −5.517 | 2.476 | 1.673 | 38.15 |
| 46 | 9.714 | 12.576 | 1.883 | 40.77 |
| 47 | −15.852 | 5.769 | | |
| 48 | ∞ | 15.658 | | |
| 49 | 131.496 | 2.156 | 1.487 | 70.24 |
| 50 | −34.585 | 5.574 | | |
| 51 | 29.722 | 10.148 | 1.834 | 37.16 |
| 52 | 12.069 | 19.375 | 1.497 | 81.55 |
| 53 | −21.137 | 23.077 | | |
| 54 | ∞ | 10.500 | 1.768 | 71.70 |
| 55 | ∞ | 2.308 | | |
| 56 (Stop) | ∞ | 0.000 | | |
| 57 | 12.430 | 2.537 | 1.497 | 81.55 |
| 58 | −27.546 | 0.512 | | |
| 59 | 6.120 | 2.568 | 1.497 | 81.55 |
| 60 | 7.393 | 1.892 | | |
| 61 | −28.281 | 0.532 | 1.699 | 30.13 |
| 62 | 4.850 | 3.842 | | |
| 63 | 11.075 | 4.794 | 1.835 | 42.71 |
| 64 | −29.957 | 6.049 | | |
| 65 | ∞ | 0.808 | 1.521 | 66.54 |
| 66 | ∞ | 0.577 | | |
| 67 | ∞ | 0.577 | 1.516 | 64.14 |
| 68 | ∞ | 0.692 | | |
| Image plane | ∞ | | | |

Aspherical surface data

3rd surface k = 0
A4 = 1.106E−02, A6 = −1.518E−03, A8 = 7.583E−05,
A10 = −2.149E−06

4th surface k = 0.012
A4 = 1.930E−02, A6 = −2.764E−03, A8 = −1.240E−03,
A10 = −5.436E−04

-continued

| Unit mm | | |
|---|---|---|
| Various data | | |
| f | | 3.00 |
| FIY | | 1.61 |
| FNO. | | 6.8 |

Aspect ratio data

| | | FIY 1.0 | FIY 0.5 | FIY 0.7 |
|---|---|---|---|---|
| | | 1.61 | 0.8 | 1.12 |
| Horizontal | 16 | 1.400 | 0.700 | 0.980 |
| Vertical | 9 | 0.788 | 0.394 | 0.551 |

Decentering data

| First optical path | | | Second optical path | | |
|---|---|---|---|---|---|
| 54th surface | | | | | |
| X | Y | Z | X | Y | Z |
| 0.00 | 0.00 | 0.00 | 0.00 | 0.00 | 0.00 |
| α | β | γ | α | β | γ |
| 0.0 | −26.3 | 0.0 | 0.0 | 26.3 | 0.0 |
| 55th surface | | | | | |
| X | Y | Z | X | Y | Z |
| 0.00 | 0.00 | 0.00 | 0.00 | 0.00 | 0.00 |
| α | β | γ | α | β | γ |
| 0.0 | −26.3 | 0.0 | 0.0 | 26.3 | 0.0 |
| from 56th surface to image plane | | | | | |
| X | Y | Z | X | Y | Z |
| 0.00 | 2.20 | 0.00 | 0.00 | −2.20 | 0.00 |
| α | β | γ | α | β | γ |
| 0.0 | 0.0 | 0.0 | 0.0 | 0.0 | 0.0 |

Surface Data

Example 2

| Unit mm | | | | |
|---|---|---|---|---|
| Surface data | | | | |
| Surface no. | r | d | nd | vd |
| Object plane | ∞ | 53.000 | | |
| 1 | ∞ | 0.820 | 1.769 | 64.15 |
| 2 | ∞ | 0.234 | | |
| 3* | 14.205 | 1.230 | 1.806 | 40.93 |
| 4* | 1.956 | 1.406 | | |
| 5 | ∞ | 18.774 | 1.806 | 40.93 |
| 6 | −8.174 | 0.442 | | |
| 7 | 11.793 | 6.564 | 1.497 | 81.55 |
| 8 | −6.378 | 0.820 | 1.847 | 23.78 |
| 9 | −19.803 | 1.593 | | |
| 10 | −7.998 | 0.586 | 1.648 | 33.79 |
| 11 | 6.148 | 11.539 | 1.883 | 40.77 |
| 12 | −29.708 | 6.807 | | |
| 13 | ∞ | 5.857 | | |
| 14 | 27.090 | 47.215 | 1.516 | 64.14 |
| 15 | ∞ | 2.767 | | |
| 16 | 32.318 | 9.534 | 1.497 | 81.55 |
| 17 | −13.115 | 1.604 | 1.755 | 52.32 |
| 18 | −27.240 | 2.343 | | |
| 19 | 27.240 | 1.604 | 1.755 | 52.32 |
| 20 | 13.115 | 9.534 | 1.497 | 81.55 |
| 21 | −32.318 | 2.767 | | |
| 22 | ∞ | 47.215 | 1.516 | 64.14 |
| 23 | −27.090 | 5.857 | | |
| 24 | ∞ | 5.857 | | |
| 25 | 27.090 | 47.215 | 1.516 | 64.14 |
| 26 | ∞ | 2.767 | | |
| 27 | 32.318 | 9.534 | 1.497 | 81.55 |
| 28 | −13.115 | 1.604 | 1.755 | 52.32 |
| 29 | −27.240 | 2.343 | | |
| 30 | 27.240 | 1.604 | 1.755 | 52.32 |
| 31 | 13.115 | 9.534 | 1.497 | 81.55 |
| 32 | −32.318 | 2.767 | | |
| 33 | ∞ | 47.215 | 1.516 | 64.14 |
| 34 | −27.090 | 5.857 | | |
| 35 | ∞ | 5.857 | | |
| 36 | 16.018 | 12.678 | 1.883 | 40.77 |
| 37 | −9.776 | 2.030 | 1.673 | 38.15 |
| 38 | 5.664 | 2.356 | | |
| 39 | 10.793 | 13.320 | 1.497 | 81.55 |
| 40 | −5.447 | 3.003 | 1.516 | 64.14 |
| 41 | −12.076 | 4.220 | | |
| 42 | 12.076 | 3.003 | 1.516 | 64.14 |
| 43 | 5.447 | 13.320 | 1.497 | 81.55 |
| 44 | −10.793 | 2.356 | | |
| 45 | −5.664 | 2.030 | 1.673 | 38.15 |
| 46 | 9.776 | 12.678 | 1.883 | 40.77 |
| 47 | −16.018 | 5.857 | | |
| 48 | ∞ | 15.896 | | |
| 49 | 84.608 | 2.385 | 1.487 | 70.24 |
| 50 | −39.702 | 5.183 | | |
| 51 | 30.446 | 5.930 | 1.834 | 37.16 |
| 52 | 12.455 | 18.700 | 1.497 | 81.55 |
| 53 | −21.254 | 23.428 | | |
| 54 | ∞ | 10.660 | 1.768 | 71.70 |
| 55 | ∞ | 2.343 | | |
| 56 (Stop) | ∞ | 1.633 | | |
| 57 | 11.217 | 2.723 | 1.497 | 81.55 |
| 58 | −39.406 | 0.468 | | |
| 59 | 6.189 | 2.563 | 1.497 | 81.55 |
| 60 | 7.530 | 1.939 | | |
| 61 | −32.416 | 0.715 | 1.699 | 30.13 |
| 62 | 4.885 | 3.327 | | |
| 63 | 11.727 | 5.322 | 1.835 | 42.71 |
| 64 | −32.637 | 5.762 | | |
| 65 | ∞ | 0.820 | 1.521 | 66.54 |
| 66 | ∞ | 0.586 | | |
| 67 | ∞ | 0.586 | 1.516 | 64.14 |
| 68 | ∞ | 0.703 | | |
| Image plane | ∞ | | | |

Aspherical surface data

3rd surface k = 0
A4 = 1.065E−02, A6 = −1.413E−03, A8 = 6.818E−05,
A10 = −1.868E−06

4th surface k = 7.414E−03
A4 = 1.893E−02, A6 = −2.463E−03, A8 = −1.038E−03,
A10 = −4.742E−04

| Various data | |
|---|---|
| f | 3.00 |
| FIY | 1.49 |
| FNO. | 6.2 |

-continued

Unit mm

Aspect ratio data

|  |  | FIY 1.0 | FIY 0.5 | FIY 0.7 |
|---|---|---|---|---|
|  |  | 1.49 | 0.75 | 1.04 |
| Horizontal | 16 | 1.3 | 0.650 | 0.910 |
| Vertical | 9 | 0.73 | 0.366 | 0.512 |

Decentering data

| First optical path | | | Second optical path | | |
|---|---|---|---|---|---|

54th surface

| X | Y | Z | X | Y | Z |
|---|---|---|---|---|---|
| 0.00 | 0.00 | 0.00 | 0.00 | 0.00 | 0.00 |
| α | β | γ | α | β | γ |
| 0.0 | −17.0 | 0.0 | 0.0 | 17.0 | 0.0 |

55th surface

| X | Y | Z | X | Y | Z |
|---|---|---|---|---|---|
| 0.00 | 0.00 | 0.00 | 0.00 | 0.00 | 0.00 |
| α | β | γ | α | β | γ |
| 0.0 | −17.0 | 0.0 | 0.0 | 17.0 | 0.0 | from 56th surface to image plane

| X | Y | Z | X | Y | Z |
|---|---|---|---|---|---|
| 0.00 | 1.60 | 0.00 | 0.00 | −1.60 | 0.00 |
| α | β | γ | α | β | γ |
| 0.0 | 0.0 | 0.0 | 0.0 | 0.0 | 0.0 |

Example 3

Unit mm

Surface data

| Surface no. | r | d | nd | vd |
|---|---|---|---|---|
| Object plane | ∞ | 45.000 | | |
| 1 | ∞ | 0.804 | 1.769 | 64.15 |
| 2 | ∞ | 0.230 | | |
| 3 | 13.454 | 1.205 | 1.806 | 40.93 |
| 4 | 1.913 | 1.377 | | |
| 5 | ∞ | 18.177 | 1.806 | 40.93 |
| 6 | −8.098 | 0.354 | | |
| 7 | 11.905 | 6.410 | 1.497 | 81.55 |
| 8 | −6.376 | 0.804 | 1.847 | 23.78 |
| 9 | −20.977 | 2.043 | | |
| 10 | −8.391 | 0.574 | 1.648 | 33.79 |
| 11 | 6.541 | 15.298 | 1.883 | 40.77 |
| 12 | −30.032 | 6.208 | | |
| 13 | ∞ | 5.739 | | |
| 14 | 25.592 | 45.631 | 1.516 | 64.14 |
| 15 | ∞ | 2.536 | | |
| 16 | 32.119 | 9.978 | 1.497 | 81.55 |
| 17 | −12.943 | 1.421 | 1.755 | 52.32 |
| 18 | −26.368 | 2.296 | | |
| 19 | 26.368 | 1.421 | 1.755 | 52.32 |
| 20 | 12.943 | 9.978 | 1.497 | 81.55 |
| 21 | −32.119 | 2.536 | | |
| 22 | ∞ | 45.631 | 1.516 | 64.14 |
| 23 | −25.592 | 5.739 | | |
| 24 | ∞ | 5.739 | | |
| 25 | 25.592 | 45.631 | 1.516 | 64.14 |
| 26 | ∞ | 2.536 | | |
| 27 | 32.119 | 9.978 | 1.497 | 81.55 |
| 28 | −12.943 | 1.421 | 1.755 | 52.32 |
| 29 | −26.368 | 2.296 | | |
| 30 | 26.368 | 1.421 | 1.755 | 52.32 |
| 31 | 12.943 | 9.978 | 1.497 | 81.55 |
| 32 | −32.119 | 2.536 | | |
| 33 | ∞ | 45.631 | 1.516 | 64.14 |
| 34 | −25.592 | 5.739 | | |
| 35 | ∞ | 5.739 | | |
| 36 | 16.074 | 12.754 | 1.883 | 40.77 |
| 37 | −9.581 | 2.584 | 1.673 | 38.15 |
| 38 | 5.228 | 2.484 | | |
| 39 | 10.741 | 12.837 | 1.497 | 81.55 |
| 40 | −5.286 | 2.960 | 1.516 | 64.14 |
| 41 | −11.626 | 2.055 | | |
| 42 | 11.626 | 2.960 | 1.516 | 64.14 |
| 43 | 5.286 | 12.837 | 1.497 | 81.55 |
| 44 | −10.741 | 2.484 | | |
| 45 | −5.228 | 2.584 | 1.673 | 38.15 |
| 46 | 9.581 | 12.754 | 1.883 | 40.77 |
| 47 | −16.074 | 5.739 | | |
| 48 | ∞ | 15.577 | | |
| 49 | 414.577 | 3.355 | 1.487 | 70.24 |
| 50 | −31.575 | 5.556 | | |
| 51 | 29.414 | 13.143 | 1.834 | 37.16 |
| 52 | 11.840 | 16.941 | 1.497 | 81.55 |
| 53 | −20.662 | 22.957 | | |
| 54 | ∞ | 10.446 | 1.768 | 71.70 |
| 55 | ∞ | 2.296 | | |
| 56 (Stop) | ∞ | 0.000 | | |
| 57 | 12.758 | 3.298 | 1.497 | 81.55 |
| 58 | −23.912 | 0.893 | | |
| 59 | 6.565 | 2.579 | 1.497 | 81.55 |
| 60 | 8.582 | 1.789 | | |
| 61 | −18.707 | 0.687 | 1.699 | 30.13 |
| 62 | 5.344 | 4.163 | | |
| 63 | 10.495 | 6.130 | 1.835 | 42.71 |
| 64 | −28.495 | 3.952 | | |
| 65 | ∞ | 0.804 | 1.521 | 66.54 |
| 66 | ∞ | 0.574 | | |
| 67 | ∞ | 0.574 | | |
| 68 | ∞ | 0.689 | 1.516 | 64.14 |
| Image plane | ∞ | | | |

Various data

| f | 3.00 |
|---|---|
| FIY | 1.78 |
| FNO. | 6.2 |

Aspect ratio data

|  |  | FIY 1.0 | FIY 0.5 | FIY 0.7 |
|---|---|---|---|---|
|  |  | 1.78 | 0.89 | 1.24 |
| Horizontal | 16 | 1.550 | 0.775 | 1.085 |
| Vertical | 9 | 0.872 | 0.436 | 0.610 |

Decentering data

| First optical path | | | Second optical path | | |
|---|---|---|---|---|---|

54th surface

| X | Y | Z | X | Y | Z |
|---|---|---|---|---|---|
| 0.00 | 0.00 | 0.00 | 0.00 | 0.00 | 0.00 |
| α | β | γ | α | β | γ |
| 0.0 | −20.0 | 0.0 | 0.0 | 20.0 | 0.0 |

-continued

Unit mm

55th surface

| X | Y | Z | X | Y | Z |
|---|---|---|---|---|---|
| 0.00 | 0.00 | 0.00 | 0.00 | 0.00 | 0.00 |
| α | β | γ | α | β | γ |
| 0.0 | −20.0 | 0.0 | 0.0 | 20.0 | 0.0 | from 56th surface to image plane

| X | Y | Z | X | Y | Z |
|---|---|---|---|---|---|
| 0.00 | 1.64 | 0.00 | 0.00 | −1.64 | 0.00 |
| α | β | γ | α | β | γ |
| 0.0 | 0.0 | 0.0 | 0.0 | 0.0 | 0.0 |

Next, values of conditional expressions in each example are given below.
Conditional Expression Example1 Example2 Example3

| Conditional Expression | Example 1 | Example 2 | Example 3 |
|---|---|---|---|
| (1) (FLBSout − FLBSin)/(FLBSout + FLBSin) | 0.00 | 0.00 | 0.00 |
| (2) Yimg/FLBSin | 0.00 | 0.00 | 0.00 |
| (3) Yimg/FLBSout | 0.00 | 0.00 | 0.00 |
| (4) Divlr/Yimgh | 1.14 | 0.17 | 0.11 |
| (5) Divs/(Divlr/2 + Yimgh) | 1.00 | 1.00 | 1.00 |
| (6) D2f/FLG1f | 1.01 | 1.00 | 1.01 |
| (7) Divs/Ds | 0.21 | 0.13 | 0.16 |
| (8) Divax/(Ds/COSΘ × SIN(θ − Θ)) | 0.99 | 1.00 | 1.00 |
| (9) ΦRLmax/Ymidimg | 1.90 | 2.57 | 1.92 |
| (10) D2b/FLG1 | 1.41 | 1.29 | 1.43 |
| (11) Ymidimg/PBSin | 0.79 | 0.48 | 0.61 |
| (12) Ymidimg/FLG1 | 0.07 | 0.06 | 0.08 |
| (13) Lss/FLG1 | 0.37 | 0.41 | 0.39 |
| (14) Yimg/FLG1 | 0.05 | 0.05 | 0.06 |
| (15) Yimg/FLG2 | 0.08 | 0.07 | 0.09 |

Values of parameters are given below.
Example1 Example2 Example3

| | Example 1 | Example 2 | Example 3 |
|---|---|---|---|
| Ds | 10.50 | 10.66 | 10.45 |
| D2b | 43.32 | 38.85 | 43.76 |
| D2f | 31.02 | 30.15 | 30.78 |
| Divax | 2.20 | 1.41 | 1.64 |
| Divs | 2.20 | 1.41 | 1.64 |
| Divlr | 1.60 | 0.22 | 0.17 |
| FLG1 | 30.76 | 30.01 | 30.53 |
| FLG1f | 30.76 | 30.01 | 30.53 |
| FLG2 | 20.59 | 21.74 | 19.94 |
| FLBSout | 1.00E+10 | 1.00E+10 | 1.00E+10 |
| FLBSin | 1.00E+10 | 1.00E+10 | 1.00E+10 |
| Lss | 11.72 | 12.54 | 12.11 |
| nBS | 1.77 | 1.77 | 1.77 |
| PBSin | 2.54 | 3.68 | 3.82 |
| Yimg | 1.61 | 1.49 | 1.78 |
| Yimgh | 1.40 | 1.3 | 1.55 |
| Ymidimg | 2.00 | 1.77 | 2.34 |
| θ | 26.30 | 17 | 20.00 |
| ΦRLmax | 3.80 | 4.55 | 4.50 |

Figure 20:
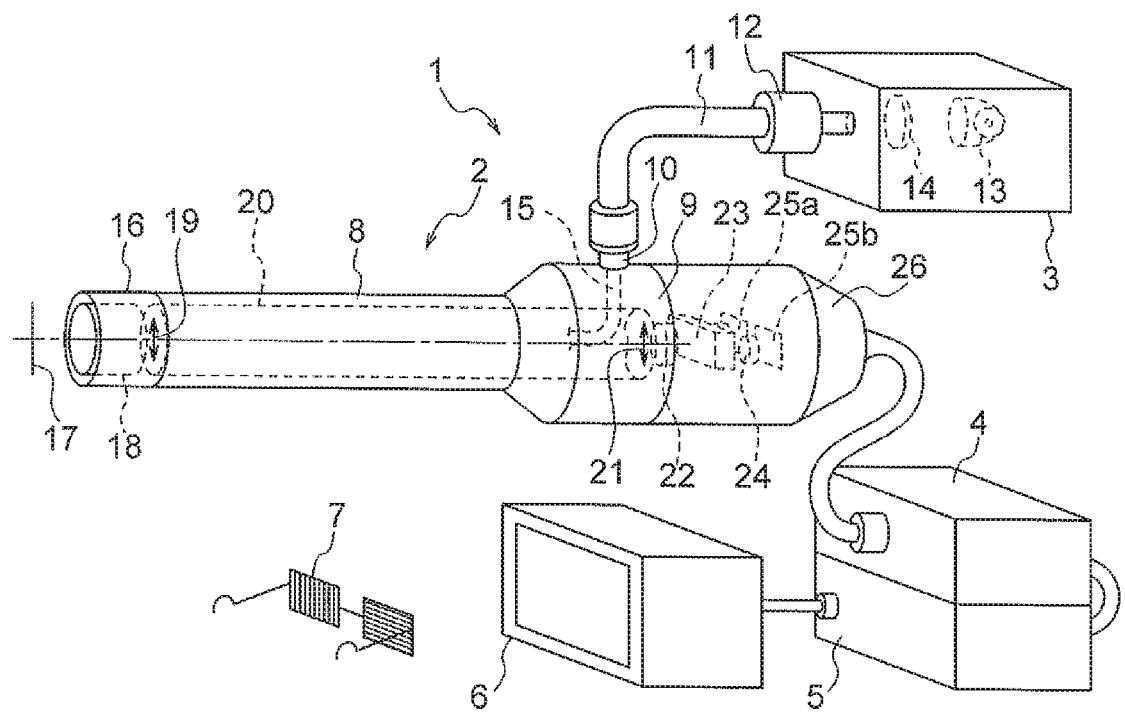
FIG. 20 is a diagram showing the stereoscopic-vision endoscope of the present embodiment.

FIG. 20 is a diagram showing the stereoscopic-vision endoscope of the present embodiment. A stereoscopic-vision endoscope 1 includes a body portion 2, a light-source unit 3, a camera control unit 4 (hereinafter, referred to as 'CCU 4'), a scan converter 5, a monitor 6, and shutter glasses 7.

The body portion 2 includes an insertion portion 8 and a holding portion 9. The insertion portion 8 is a portion to be inserted into a body cavity, and is formed by a hard jacket tube. The jacket tube is in the form of a circular tube, and is made of a metal such as stainless steel. In such manner, the stereoscopic-vision endoscope 1 is a rigid endoscope. The holding portion 9 is a portion to be held by an operator.

The holding portion 9 is provided with a light-guide tube 10. One end of a light-guide cable 11 is connected to the light-guide tube 10. The other end of the light-guide cable 11 is provided with alight-guide connector 12. The light-guide cable 11 is detachably connected to the holding portion 9 and the light-source unit 3.

The light-source unit 3 includes a lamp 13 and a lens 14. The lamp 13 generates illumination light such as white light. The lens 14 focuses the illumination light. The illumination light focused by the lens 14 is irradiated to an end surface of the light-guide connector 12. The illumination light irradiated to the end surface is transmitted to the body portion 2 by a light guide inside the light-guide cable 11.

The body portion 2 is provided with a light guide 15. The light guide 15 is bent inside the holding portion 9, and is passed through the insertion portion 8. The light guide 15 transmits the illumination light supplied from the light-guide cable 11 to a front-end surface which is fixed to a front-end portion 16 of the insertion portion 8. Accordingly, the illumination light is emerged frontward from the front-end surface.

An object 17 is illuminated by the illumination light. Light from the object 17 is incident on an objective optical system 18 which is disposed inside the front-end portion 16. An optical image 19 is formed at an image forming position of the objective optical system 18. The optical image 19 is relayed to the holding portion 9 by a relay optical system 20.

An intermediate image 21 is formed at a rearmost position of the relay optical system 20. The intermediate image 21 is re-formed by a first lens unit 22, a light-beam splitting element 23, and a second lens unit 24. Accordingly, a first image is formed on an image pickup surface of a first image pickup element 25a, and a second image is formed on an image pickup surface of a second image pickup element 25b.

One end of a signal cable 27 is connected to an output portion 26. The other end of the signal cable 27 is connected to the CCU 4. A signal which is output from the first image pickup element 25a and a signal which is output from the second image pickup element 25b are input to the CCU 4 via the signal cable 27.

In the CCU 4, signal processing is carried out on signals output from the first image pickup element 25a and the second image pickup element 25b. An image signal subjected to signal processing in the CCU 4 is input to the scan converter 5. In the scan converter 5, the signal output from the CCU 4 is converted to a video signal.

The video signal is input to the monitor 6. The monitor 6 displays the video signal that has been input. Two images having a parallax are displayed alternately on the monitor 6. The shutter glasses 7 have a shutter function. By using the shutter glasses, images displayed on the monitor 6 can be viewed stereoscopically.

According to the present embodiment, it is possible to provide a stereoscopic-vision endoscope which has the favorable resolution performance, while having a small size.

As described heretofore, the present invention is suitable for a stereoscopic-vision endoscope which has the favorable resolution performance, while having a small size.

What is claimed is:

1. A stereoscopic-vision endoscope, comprising in order from an object side:
an objective optical system;
a relay optical system;
a first lens unit;
a light-beam splitting element;
a second lens unit; and
an image sensor, wherein
the objective optical system, the relay optical system, the first lens unit, and the light-beam splitting element are disposed in a common optical path, and
a first optical path and a second optical path are formed on an image side of the light-beam splitting element, by the light-beam splitting element, and
the second lens unit is disposed in each of the first optical path and the second optical path, and
an image of an object is formed by the objective optical system, and
the image of the object is relayed by the relay optical system, and
an intermediate image is formed on the object side of the first lens unit by the relay optical system, and
a first image is formed by the first lens unit and the second lens unit which is disposed in the first optical path, and
a second image is formed by the first lens unit and the second lens unit which is disposed in the second optical path, and
the first image and the second image are captured by the image sensor, and
the light-beam splitting element has a surface of incidence and a surface of emergence, and
a first light ray which passes through a center of the intermediate image and reaches a center of the first image, and a second light ray which passes through the center of the intermediate image and reaches a center of the second image are refracted to be away from an optical axis of the common optical path on the surface of incidence, as well as are refracted to be closer to the optical axis of the common optical path on the surface of emergence.

2. The stereoscopic-vision endoscope according to claim 1, wherein the following conditional expression (1) is satisfied:

$$-0.1 \leq (FLBSout-FLBSin)/(FLBSout+FLBSin) \leq 0.1 \quad (1)$$

where,
FLBSin denotes a focal length at the surface of incidence of the light-beam splitting element, and
FLBSout denotes a focal length at the surface of emergence of the light-beam splitting element.

3. The stereoscopic-vision endoscope according to claim 1, wherein the following conditional expressions (2) and (3) are satisfied:

$$-0.01 \leq Yimg/FLBSin \leq 0.01 \quad (2)$$

$$-0.01 \leq Yimg/FLBSout \leq 0.01 \quad (3)$$

where,
FLBSin denotes a focal length at the surface of incidence of the light-beam splitting element, and
FLBSout denotes a focal length at the surface of emergence of the light-beam splitting element, and
Yimg denotes the maximum image height.

4. The stereoscopic-vision endoscope according to claim 1, wherein the image sensor has a first effective area capturing the first image, and a second effective area capturing the second image, and
the following conditional expression (4) is satisfied:

$$0.05 \leq Divlr/Yimgh \leq 2 \quad (4)$$

where,
Divlr denotes the minimum distance between the first effective area and the second effective area, and
Yimgh denotes a predetermined image height, and here
the minimum distance is a distance which is the smallest distance between a point on an outer periphery of the first effective area and a point on an outer periphery of the second effective area,
the predetermined image height is a height when the maximum image height is projected in a parallax direction,
the distance is a distance in the parallax direction, and
the parallax direction is a direction orthogonal to both of an optical axis of the first optical path and an optical axis of the second optical path.

5. The stereoscopic-vision endoscope according to claim 1, wherein an aperture stop is disposed between the first lens unit and the light-beam splitting element or between the light-beam splitting element and the second lens unit.

6. The stereoscopic-vision endoscope according to claim 1, wherein the following conditional expression (5) is satisfied:

$$0.7 \leq Divs/(Divlr/2+Yimgh) \leq 1.3 \quad (5)$$

where,
Divs denotes a distance between a point of incidence and a point of emergence,
Divlr denotes the minimum distance between the first effective area and the second effective area, and
Yimgh denotes a predetermined image height, and here
the point of incidence is a point of intersection of the first light ray and the surface of incidence,
the point of emergence is a point of intersection of the first light ray and the surface of emergence,
the minimum distance is a distance which is the smallest distance between a point on an outer periphery of the first effective area and a point on an outer periphery of the second effective area,
the predetermined image height is a height when the maximum image height is projected in a parallax direction,
the distance is a distance in the parallax direction, and
the parallax direction is a direction orthogonal to both of an optical axis of the first optical path and an optical axis of the second optical path.

7. The stereoscopic-vision endoscope according to claim 1, wherein the following conditional expression (6) is satisfied:

$$0.8 \leq D2f/FLG1f \leq 1.2 \quad (6)$$

where,
D2f denotes a distance on an optical axis of the common optical path, between a position of a principal point on the object side of the first lens unit and the intermediate image, and
FLG1f denotes an object-side focal length of the first lens unit.

8. The stereoscopic-vision endoscope according to claim 1, wherein both the first light ray emerged from the surface of emergence and the second light ray emerged from the surface of emergence are parallel to the optical axis of the common optical path.

9. The stereoscopic-vision endoscope according to claim 1, wherein the surface of incidence and the surface of emergence have a shape such that a distance from the optical axis of the common optical path increases toward the object side from a point of intersection of the optical axis of the common optical path.

10. The stereoscopic-vision endoscope according to claim 1, wherein the following conditional expression (7) is satisfied:

$$0.05 \leq Divs/Ds \leq 0.7 \quad (7)$$

where,
Divs denotes a distance between a point of incidence and a point of emergence, and
Ds denotes a distance between the surface of incidence and the surface of emergence, and here
the point of incidence is a point of intersection of the first light ray and the surface of incidence,
the point of emergence is a point of intersection of the first light ray and the surface of emergence,
the distance is a distance in the parallax direction, and
the parallax direction is a direction orthogonal to both of an optical axis of the first optical path and an optical axis of the second optical path.

11. The stereoscopic-vision endoscope according to claim 1, wherein the following conditional expression (8) is satisfied:

$$0.85 \leq Divax/(Ds/\cos\Theta \times \sin(\theta-\Theta)) \leq 1.15 \quad (8)$$

where,
$\Theta = A\sin((1/nBS) \times \sin\theta)$,
Divax denotes a distance between the optical axis of the common optical path and an optical axis of the first optical path,
Ds denotes a distance between the surface of incidence and the surface of emergence,
$\theta$ denotes an angle made by a surface orthogonal to the optical axis of the common optical path and the surface of incidence,
nBS denotes a refractive index of the light-beam splitting element for a d-line,
the point of incidence is a point of intersection of the first light ray and the surface of incidence,
the point of emergence is a point of intersection of the first light ray and the surface of emergence,
the distance is a distance in the parallax direction, and
the parallax direction is a direction orthogonal to both of an optical axis of the first optical path and an optical axis of the second optical path.

12. The stereoscopic-vision endoscope according to claim 1, wherein the following conditional expression (9) is satisfied:

$$0.6 \leq \Phi RL\,max/Ymidimg \leq 3.5 \quad (9)$$

Where,
$\Phi RLmax$ denotes the maximum lens diameter of the relay optical system, and
Ymidimg denotes the maximum image height of the intermediate image.

13. The stereoscopic-vision endoscope according to claim 1, wherein the following conditional expression (10) is satisfied:

$$0.6 \leq \Phi RL\,max/Ymidimg \leq 3.5 \quad (9)$$

where,
D2b denotes a distance on the optical axis of the common optical path, between a position of a principal point on an image side of the first lens unit and the light-beam splitting element, and
FLG1 denotes a focal length of the first lens unit.

14. The stereoscopic-vision endoscope according to claim 1, wherein the following conditional expression (11) is satisfied:

$$0.2 \leq Ymidimg/PBSin \leq 1.2 \quad (11)$$

where,
Ymidimg denotes the maximum image height of the intermediate image, and
PBSin denotes a height of an effective light ray incident on the light-beam splitting element.

15. The stereoscopic-vision endoscope according to claim 1, wherein the following conditional expression (12) is satisfied:

$$0.01 \leq Ymidimg/FLG1 \leq 0.2 \quad (12)$$

where,
Ymidimg denotes the maximum image height of the intermediate image, and
FLG1 denotes a focal length of the first lens unit.

16. The stereoscopic-vision endoscope according to claim 1, wherein
a predetermined pupil is a pupil that is formed at a position nearest to the intermediate image, on the object side of the intermediate image, and
the light-beam splitting element is disposed at a position conjugate with the predetermined pupil.

17. The stereoscopic-vision endoscope according to claim 1, wherein
an aperture stop is disposed on the image side of the intermediate image, and
a shape of an opening portion of the aperture stop is a circular shape.

18. The stereoscopic-vision endoscope according to claim 1, wherein
an aperture stop is disposed on the image side of the intermediate image, and
a shape of an opening portion of the aperture stop is a shape having different lengths in two directions that are orthogonal, and
one of the two directions is a parallax direction and the other direction is a direction orthogonal to the parallax direction.

19. The stereoscopic-vision endoscope according to claim 1, wherein
an aperture stop is disposed on the image side of the intermediate image, and
the following conditional expression (13) is satisfied:

$$0 < Lss/FLG1 \leq 0.8 \quad (13)$$

where,
Lss denotes a distance on the optical axis of the common optical path, between the surface of incidence and the aperture stop, and
FLG1 denotes a focal length of the first lens unit.

20. The stereoscopic-vision endoscope according to claim 1, wherein the following conditional expression (14) is satisfied:

$$0.01 \leq Yimg/FLG1 \leq 0.2 \quad (14)$$

where,
Yimg denotes the maximum image height, and
FLG1 denotes a focal length of the first lens unit.

21. The stereoscopic-vision endoscope according to claim 1, wherein the following conditional expression (15) is satisfied:

$$0.01 \leq Yimg/FLG2 \leq 0.5 \qquad (15)$$

where,
Yimg denotes the maximum image height, and
FLG2 denotes a focal length of the second lens unit.

22. The stereoscopic-vision endoscope according to claim 1, wherein
the first lens unit includes a plurality of lenses, and
at the time of focusing, at least some lenses of the plurality of lenses move along the optical axis of the common optical path.

23. The stereoscopic-vision endoscope according to claim 1, wherein
the second lens unit includes a plurality of lenses, and
at the time of focusing, at least some lenses of the plurality of lenses move along an optical axis of the first optical path or an optical axis of the second optical path.

24. The stereoscopic-vision endoscope according to claim 1, wherein
the image sensor includes a first image pickup area which is positioned in the first optical path and a second image pickup area which is positioned in the second optical path, and
a distance between a center of the first image pickup area and a center of the second image pickup area is longer than a distance between an optical axis of the first optical path and an optical axis of the second optical path.

25. The stereoscopic-vision endoscope according to claim 1, wherein a flare aperture which shields light rays other than an effective light ray, is positioned on the image side of the intermediate image.

* * * * *